United States Patent [19]

Furutachi et al.

[11] Patent Number: 4,929,540

[45] Date of Patent: May 29, 1990

[54] SILVER HALIDE COLOR PHOTOGRAPHIC LIGHT-SENSITIVE MATERIAL

[75] Inventors: Nobuo Furutachi; Takeshi Hirose, both of Minami-ashigara, Japan

[73] Assignee: Fuji Photo Film Co., Ltd., Kanagawa, Japan

[21] Appl. No.: 380,489

[22] Filed: Jul. 17, 1989

[30] Foreign Application Priority Data

Jul. 18, 1988 [JP] Japan .................. 63-178486

[51] Int. Cl.$^5$ ................................ G03C 1/08
[52] U.S. Cl. .................................. 430/555; 430/544; 430/387
[58] Field of Search .................. 430/555, 544, 387

[56] References Cited

U.S. PATENT DOCUMENTS

| | | | |
|---|---|---|---|
| 4,351,897 | 9/1982 | Aoki et al. | 430/555 |
| 4,383,027 | 5/1983 | Ishikawa et al. | 430/387 |
| 4,483,918 | 11/1984 | Sakai et al. | 430/555 |
| 4,556,630 | 12/1985 | Furutachi et al. | 430/555 |
| 4,584,266 | 4/1986 | Hirose et al. | 430/555 |

*Primary Examiner*—Richard L. Schilling
*Assistant Examiner*—Thomas R. Neville
*Attorney, Agent, or Firm*—Birch, Stewart, Kolasch & Birch

[57] ABSTRACT

A silver halide color photographic light-sensitive material comprising a support and at least one silver halide photographic emulsion layer on the support, said emulsion layer containing a 5-pyrazolone coupler having a coupling eliminable group of the following general formula (I) at the coupling site thereof:

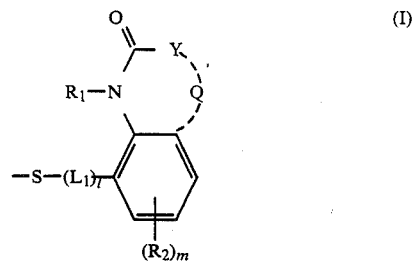

wherein $L_1$ represents a substituted or an unsubstituted methylene or ethylene group; l represents 0 or 1; m represents 0 or an integer from 1 to 3; $R_1$ represents a hydrogen atom, or a substituted or an unsubstituted alkyl, aryl or heterocyclic group; Y represents

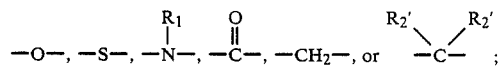

Q represents a single bond or nonmetal atoms necessary to complete a 5- to 8-membered ring together with

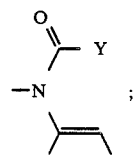

said 5- to 8-membered ring may further have a saturated or an unsaturated ring condensed thereto; $R_2$ represents a halogen atom, an alkyl group; an aryl group, an alkoxy group, an aryloxy group, an alkylthio group, an arylthio group, an alkylsulfonyl group, an arylsulfonyl group, an acylamino group, an alkoxycarbonylamino group, a sulfonamide group, a sulfamoyl group, an ureido group, an alkoxycarbonyl group, an aryloxycarbonyl group, an acyl group, a cyano group, a trifluoromethyl group, an amino group, an N-alkylamino group, an N-arylamino group, an N,N-dialkylamino group, a diacylamino group, an imido group or a carbamoyl group, and when m represents 2 or 3, $R_2$ groups may be the same or different; $R_2'$ represents a hydrogen atom, or has the same meaning as $R_2$ and two $R_2'$ groups may be linked to form a 5- to 7-membered saturated or unsaturated ring; and —Y Q may be a substituted or an unsubstituted carbon-carbon or carbon-nitrogen double bond. The silver halide photographic material provides a magenta image having a high maximum density and light fastness.

7 Claims, No Drawings

SILVER HALIDE COLOR PHOTOGRAPHIC LIGHT-SENSITIVE MATERIAL

FIELD OF THE INVENTION

The present invention relates to a silver halide color photographic light-sensitive material containing a novel pyrazolone magenta color image forming coupler and, more particularly, to a silver halide color photographic light-sensitive material containing a novel mercaptane-releasing two-equivalent pyrazolone magenta color image forming coupler which can produce a sufficiently high density of a magenta color even in rapid development-processing.

BACKGROUND OF THE INVENTION

U.S. Pat. No. 3,227,554 discloses that in the development-processing of color photographic light-sensitive materials, pyrazolone couplers having an arylthio group at their respective coupling sites produce a sufficient color density as the magenta color image forming coupler. The couplers disclosed in the above patent are markedly inferior in light fastness of the magenta color image formed therefrom through photographic processing. On the other hand, magenta color images formed from pyrazolone couplers having an alkoxy group introduced at the position ortho to the phenylthio coupling eliminable group, which are disclosed in U.S. Pat. No. 4,351,897 and U.S. B-1 4,351,897, have a considerably improved fastness to light.

Increasing the processing speed in color development is a recent trend. For instance, processing solutions as described in WO-87/4534 are proposed for this purpose. However, pyrazolone couplers having a phenylthio group as a splitting group, and an alkoxy group at the ortho position, tend to produce a somewhat lowered color density when developed with the above-described processing solutions.

Under these circumstances, it has been strongly desired to design the magenta couplers with an arylthio group at the coupling active site so that the color images produced therefrom can have not only a sufficiently high fastness to light, but also a high maximum density even in rapid color development, particularly in color development having a processing time shortened to 2 minutes or less.

SUMMARY OF THE INVENTION

Therefore, an object of the present invention is to provide a silver halide color photographic light-sensitive material which produces a color image having a sufficiently high fastness to light after color development.

Another object of the present invention is to provide a silver halide color photographic light-sensitive material which ensures a sufficiently high maximum density of the magenta color in rapid development-processing.

The above-described objects are attained with a silver halide color photographic light-sensitive material comprising a support having thereon at least one silver halide emulsion layer containing a 5-pyrazolone coupler having a coupling eliminable group represented by the following general formula (I) at the coupling site thereof:

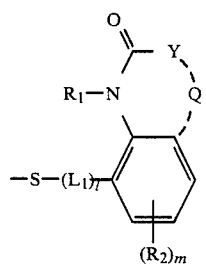

wherein $L_1$ represents a substituted or an unsubstituted methylene or ethylene group; l represents 0 or 1; m represents 0 or an integer from 1 to 3; $R_1$ represents a hydrogen atom, or a substituted or an unsubstituted alkyl, aryl or heterocyclic group; Y represents $$-O-, -S-, -N-, -C-, -CH_2-, \text{ or } -C- ;$$
$$\phantom{-O-, -S-, }\overset{|}{R_1}\phantom{-, }\overset{\|}{O}\phantom{-, -CH_2-, or }\overset{R_2'}{\underset{R_2'}{\diagup}}$$

Q represents a single bond or nonmetal atoms necessary to complete a 5- to 8-membered ring together with

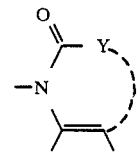

said 5- to 8-membered ring may further has a saturated or an unsaturated ring condensed thereto; $R_2$ represents a halogen atom, an alkyl group, an aryl group, an alkoxy group, an aryloxy group, an alkylthio group, an arylthio group, an alkylsulfonyl group, an arylsulfonyl group, an acylamino group, an alkoxycarbonylamino group, a sulfonamido group, a sulfamoyl group, an ureido group, an alkoxycarbonyl group, an aryloxycarbonyl group, an acyl group, a cyano group, a trifluoromethyl group, an amino group, an N-alkylamino group, an N-arylamino group, an N,N-dialkylamino group, a diacylamino group, an imido group or a carbamoyl group, and when m represents 2 or 3, $R_2$ groups may be the same or different; $R_2'$ represents a hydrogen atom, or has the same meaning as $R_2$ and two $R_2'$ groups may abe linked to form a 5- to 7-membered saturated or unsaturated ring; and —Y—Q— may be a substituted or an unsubstituted carbon-carbon or carbon-nitrogen double bond.

DETAILED DESCRIPTION OF THE INVENTION

The substituent groups in general formula (I) above are illustrated in detail below.

In the present invention, where the acyl group, the acylamino group, the sulfonyl group, the sulfonamido group, the sulfamido group, etc., are not specifically defined, they include aliphatic and aromatic groups thereof.

With regard to the substituent groups of the methylene or ethylene groups represented by $L_1$, and the substituent groups of the alkyl, aryl or heterocyclic groups represented by $R_1$, the substituent groups include the same groups as defined in $R_2$. The heterocyclic group is preferably a 5- to 7-membered heterocyclic group containing at least one of N, O and S as a hetero atom.
Specific examples of a ring system in general formula (I) are illustrated below.
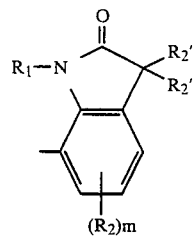
(1)
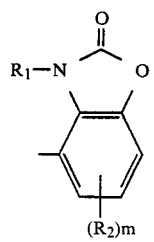
(2)
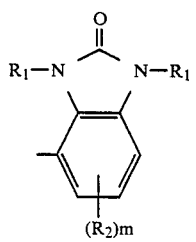
(3)
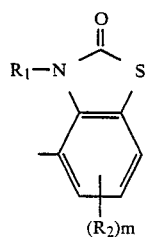
(4)
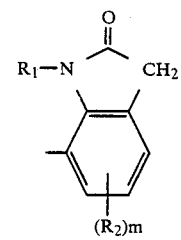
(5)
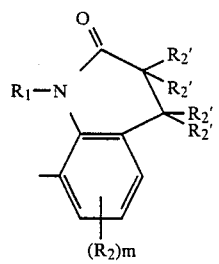
(6)
-continued
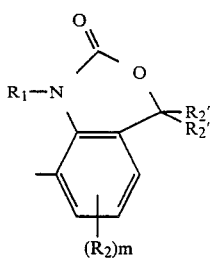
(7)
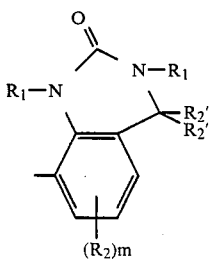
(8)
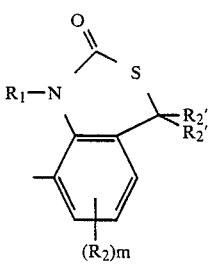
(9)
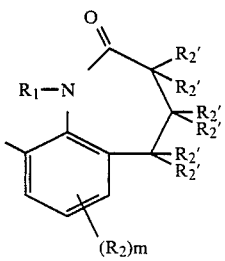
(10)
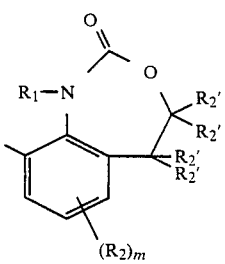
(11)
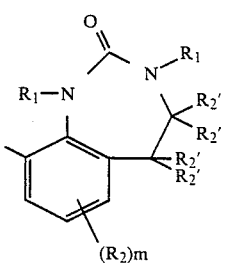
(12)

4,929,540
-continued
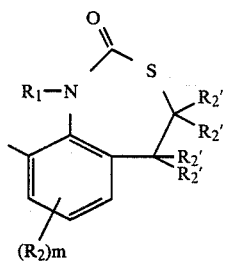
(13)
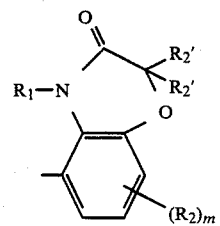
(14)
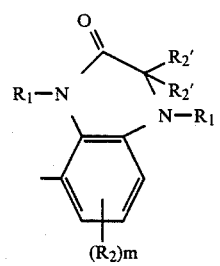
(15)
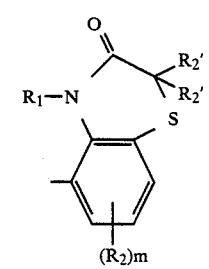
(16)
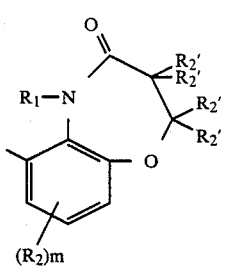
(17)
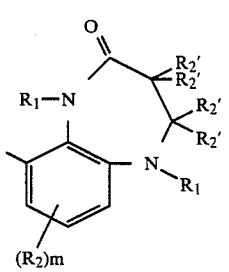
(18)
-continued
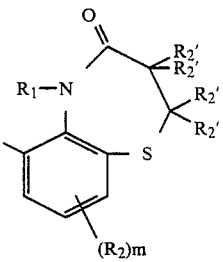
(19)
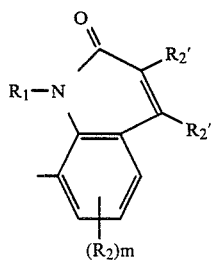
(20)
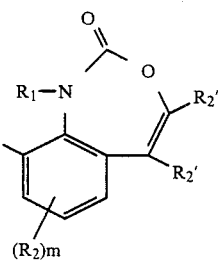
(21)
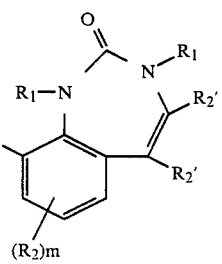
(22)
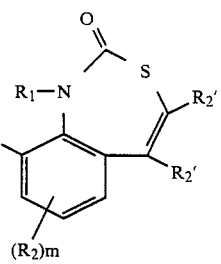
(23)
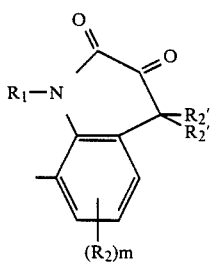
(24)

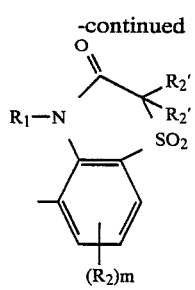

(25)

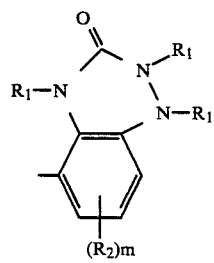

(26)

wherein each symbols are the same as defined hereinabove.

R₂ is described in detail. R₂ represents a halogen atom (e.g., fluorine, chlorine, bromine), an alkyl group (e.g., methyl, ethyl, n-butyl, t-butyl, t-octyl, dodecyl, 2-ethylhexyl, 2-dodecyloxyethyl, 3-(2,4-di-tert-amylphenoxy)propyl, 2,2-dimethyl-2-(3-pentadecylphenoxy)ethyl), an aryl group (e.g., phenyl, α- or β-naphthyl, 2,4-dichlorophenyl, 2-methoxyphenyl, 4-dodecyloxyphenyl, 2-chloro-5-tetradecanephenyl), an alkoxy group (e.g., methoxy, ethoxy, 2-dodecyloxyethoxy, 3-phenoxypropoxy, 2-ethoxyethoxy, octyloxy, 2-ethylhexyloxy, 2-(2,4-di-tert-pentylphenoxy)ethoxy), an aryloxy group (e.g., phenoxy, α- or β-naphthoxy, 4-tert-butylphenoxy), an alkylthio group (e.g., methylthio, butylthio, octylthio, α-dodecyloxycarbonylpropylthio, 3-phenoxypropylthio, 2-butoxycarbonylethylthio), an arylthio group (e.g., phenylthio, 4-tert-butylphenylthio, 2-butoxy-5-tert-octylphenylthio, 4-dodecyloxyphenylthio), an alkylsulfonyl group (e.g., methanesulfonyl, ethanesulfonyl, octanesulfonyl, dodecanesulfonyl), an arylsulfonyl group (e.g., benzenesulfonyl, toluenesulfonyl, 4-hydroxyphenylsulfonyl, 2-butoxy-5-tert-octylphenylsulfonyl), an acylamino group (e.g., acetamido, 2-ethylhexanoylamido, hexadecanamido, α-(2,4-di-tert-pentylphenoxy)acetamido, benzamido, 3-(2-ethylhexanamido)benzamido, 2-pyridinecarbonamido, 2-chloro-4-t-hexylbenzamido), an alkoxycarbonylamino group (e.g., ethoxycarbonylamino, t-butoxycarbonylamino, 2-methylpropyloxycarbonylamino), a sulfonamido group (e.g., methanesulfonamido, butanesulfonamido, benzenesulfonamido, 2-butoxy-5-tert-octylbenzenesulfonamido, 4-dodecyloxybenzenesulfonamido) group, a sulfamoyl group (e.g., N-methylsulfamoyl, N,N-diethylsulfamoyl, N-tert-butylsulfamoyl, 3-(2,4-di-tert-pentylphenoxy)propylsulfamoyl), an ureido group (e.g., phenylureido, 4-cyanophenylureido, tetradecylureido, 4-ethanesulfonylphenylureido), an alkoxycarbonyl group (e.g., ethoxycarbonyl, dodecyloxycarbonyl, benzyloxycarbonyl, 2-methylpropyloxycarbonyl), an aryloxycarbonyl group (e.g., phenoxycarbonyl, 2,4-di-tert-butylphenoxycarbonyl), an acyl group (e.g., acetyl, benzoyl, dodecanoyl, α-(2,4-di-tert-pentylphenoxy)acetyl, a cyano group, a trifluoromethyl group, an amino group, an N-arylamino group (e.g., anilino, 2,4-dichloroanilino, 4-methoxyanilino, 2-chloro-5-tetradecaneanilino, 3-acetamidoanilino, 4-tert-octylanilino, α- or β-naphthylamino), an N,N-dialkylamino group (e.g., N,N-diethylamino, N-ethyl-N-dodecylamino, N,N-bis(2-dodecyloxyethylamino)), a diacylamino group (e.g., N,N-diacetylamino, N-acetyl-N-benzamido), an imido group (e.g., succinimido, phthalimido, glutarimido, 1-benzyl-5,5-dimethyl-3-hydantoinyl, 5,5-dimethyl-2,4-dioxo-3-oxazolidinyl), or a carbamoyl group (e.g., N-ethylcarbamoyl, N-[3-2,4-di-tert-pentylphenoxy)propyl]carbamoyl, N-ethyl-N-dodecylcarbamoyl, N-tert-octylcarbamoyl).

Among the coupling eliminable groups represented by the general formula (I), those satisfying the condition of l=0 and R₁=hydrogen atom are particularly preferred.

The 5-pyrazolone coupler to be used in the present invention is represented by the following general formula (II):

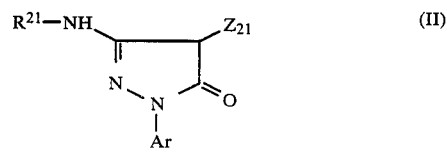

(II)

wherein $R^{21}$ represents an alkyl group, an aryl group, an acyl group, or a carbamoyl group; Ar represents a phenyl group, or a phenyl group substituted by at least one halogen atom, alkyl group, cyano group, alkoxy group, alkoxycarbonyl group or acylamino group; and $Z_{21}$ represents a thio group of the general formula (I).

In general formula (II), an alkyl group represented by $R^{21}$ includes those containing 1 to 42 carbon atoms, such as methyl, butyl, octadecyl, 2-(2,4-di-tert-amylphenoxy)ethyl, etc.; an aryl group represented by $R^{21}$ includes, for example, phenyl, 2-chlorophenyl, 2-chloro-5-tetradecanephenyl, 2-chloro-5-(3-octadecenyl-N-succinimido)phenyl, 2-chloro-5-[α-(4-hydroxy-3-tert-butylphenoxy)tetradecanamido]phenyl, 2,4-dichloro-5-dodecyloxyphenyl, 2-chloro-5-octadecylthiophenyl, and so on; an acyl group represented by $R^{21}$ includes, for example, acetyl, 2-ethylhexanoyl, α-(2,4-di-tert-pentylphenoxy)acetyl, α-(2,4-di-tert-pentylphenoxy)butanoyl, γ-(2,4-di-tert-pentylphenoxy)butanoyl, α-(3-pentadecylphenoxy)butanoyl, and so on; and a carbamoyl group represented by $R^{21}$ includes, for example, N-methylcarbamoyl, N,N-dimethylcarbamoyl, N-hexadecylcarbamoyl, N-methyl-N-phenylcarbamoyl, N-{3-[α-(2,4-di-tert-pentylphenoxy)butylamido]}phenylcarbamoyl, and so on. It is preferred that R₁ contains a ballast group to make the coupler or the dye obtained from the coupler immobile in the photographic layer. For this purpose the carbon number of the ballast group is preferably at least 8, and more preferably at least 13. Furthermore, the ballast group may be a polymer.

Suitable examples of groups represented by Ar include phenyl, 2,4,6-trichlorophenyl, 2,5-dichlorophenyl, 2,4-dimethyl-6-methoxyphenyl, 2,6-dichloro-4-methoxyphenyl, 2,6-dichloro-4-ethoxycarbonylphenyl, 2,6-dichloro-4-cyanophenyl, 4-[α-(2,4-di-tert-amylphenoxy)butylamido]phenyl, and so on.

Among the pyrazolone mother nuclei of general formula (II), those containing an aryl group as $R^{21}$ are particularly preferred.

The coupler of the present invention may be in the form of a compound containing one moiety of the coupler, a biscompound of the coupler containing two moieties of the coupler, or a polymer wherein the coupler moieties are bonded to the polymer chain through the substituent group on the pyrazolone skeleton or through a substituent group of eliminable group.

Specific examples of the couplers to be employed in the present invention are illustrated below. However, the invention should not be construed as being limited to these representative examples.

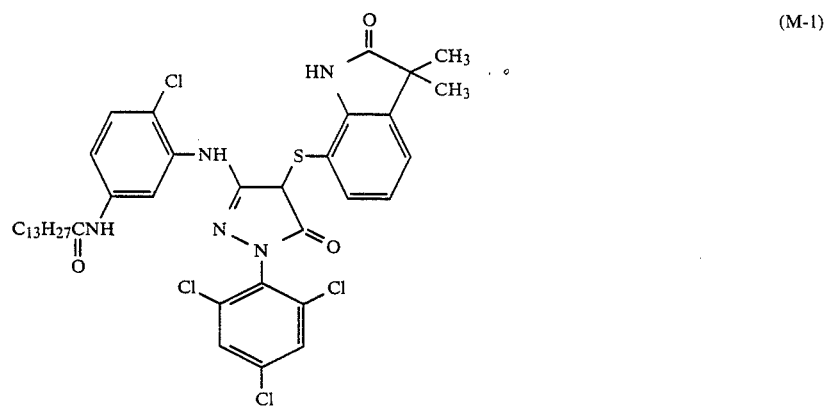
(M-1)

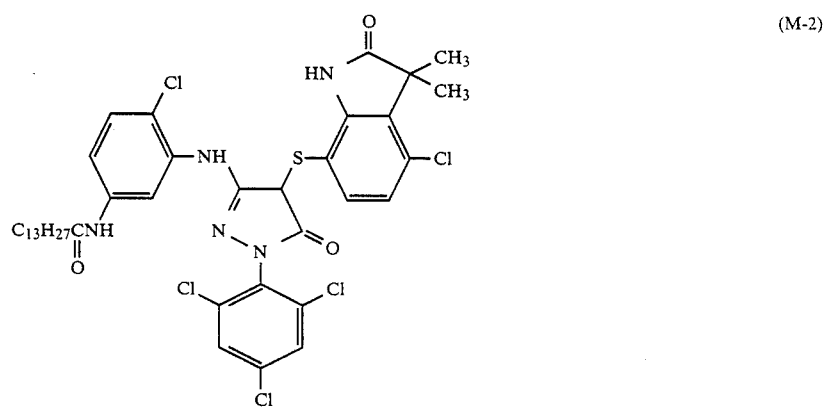
(M-2)

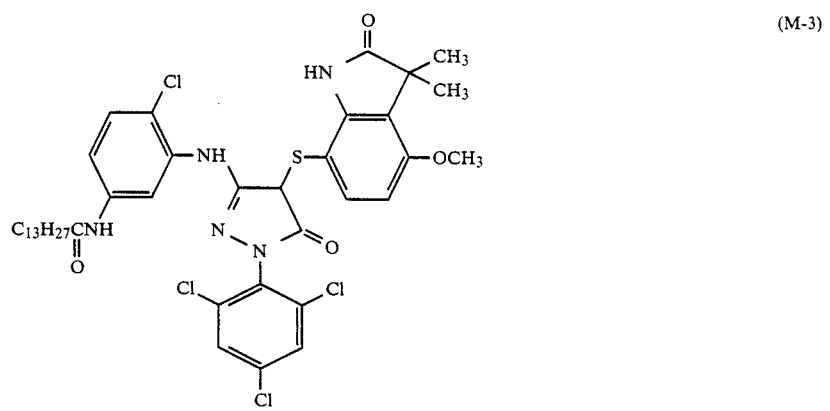
(M-3)

-continued
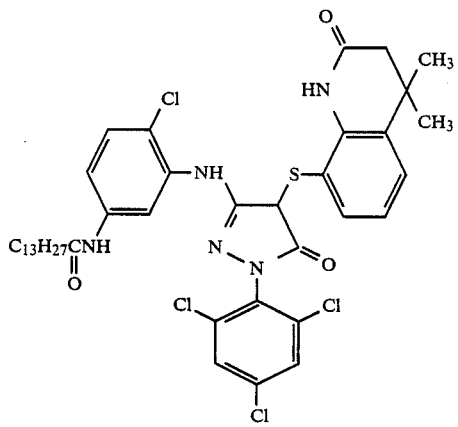
(M-4)
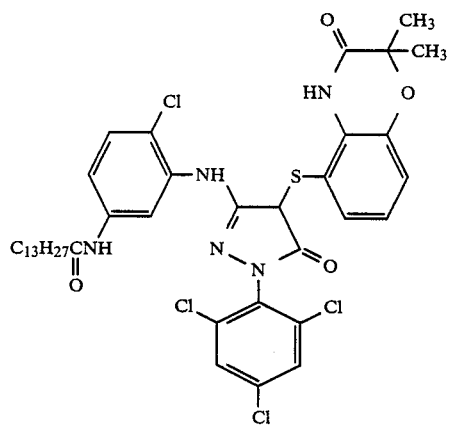
(M-5)
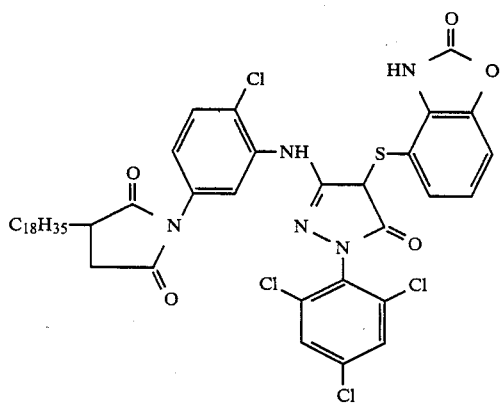
(M-6)
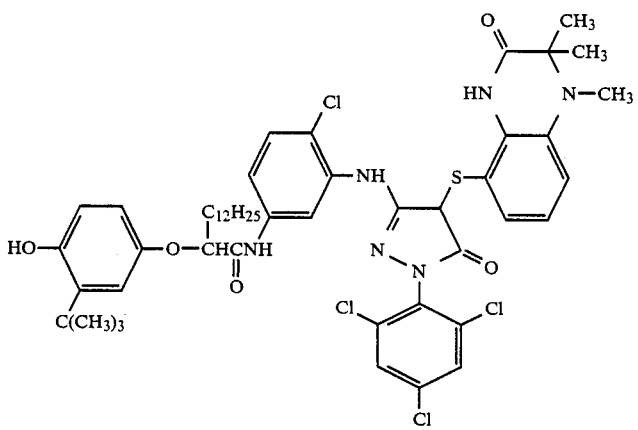
(M-7)

(M-8)
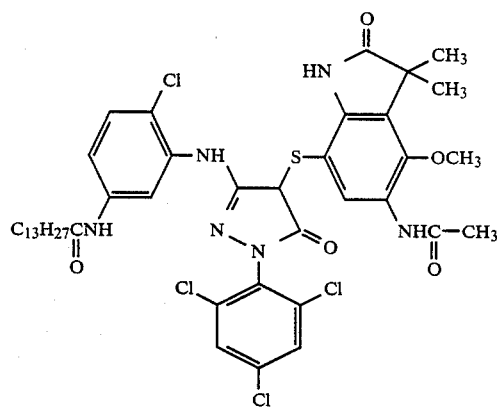
(M-9)
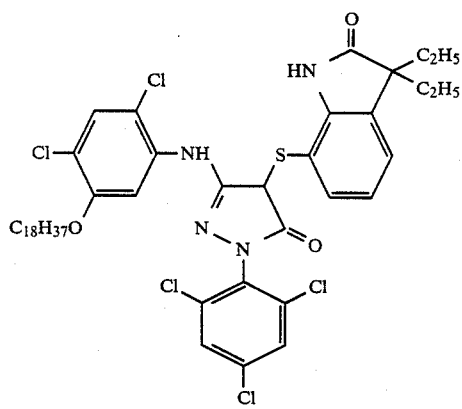
(M-10)
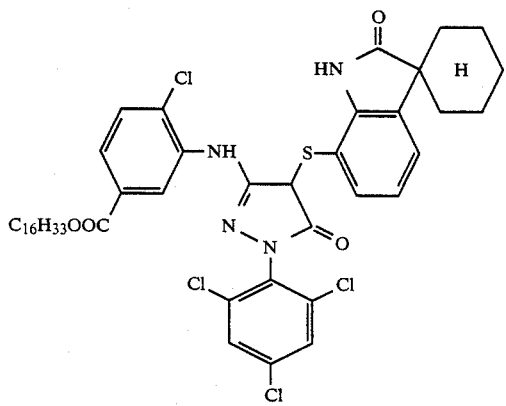
(M-11)
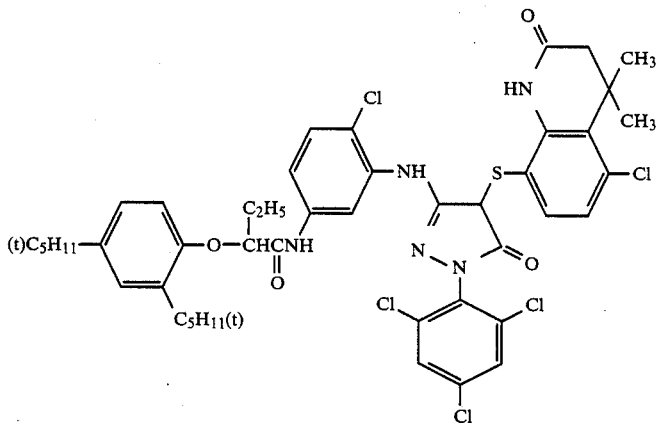

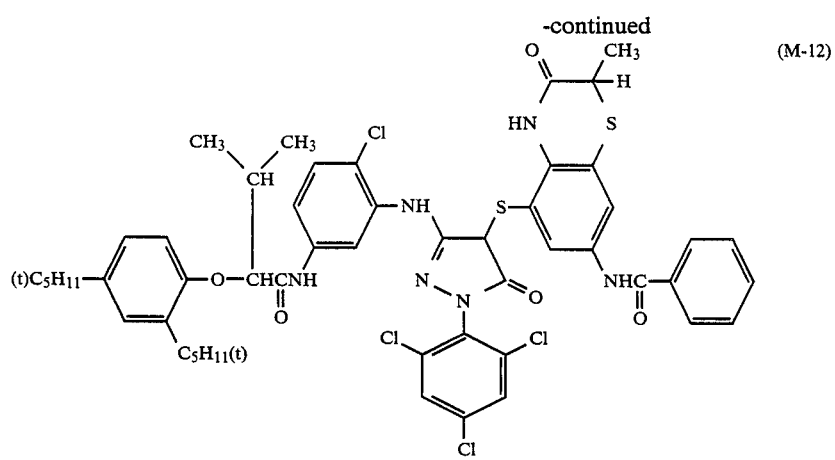
(M-12)
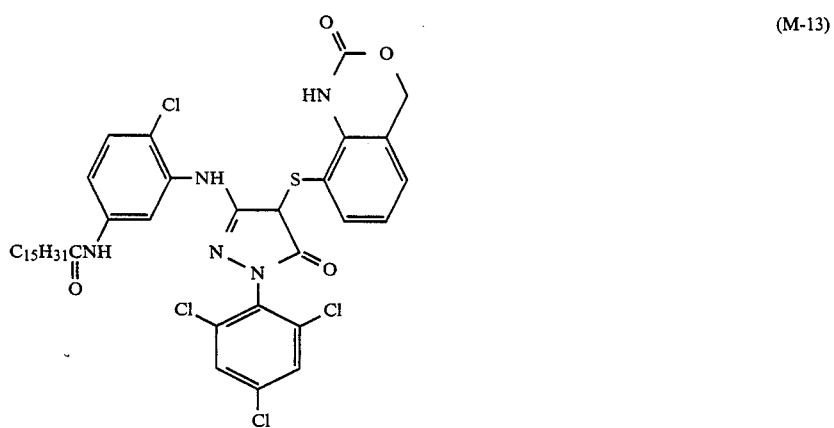
(M-13)
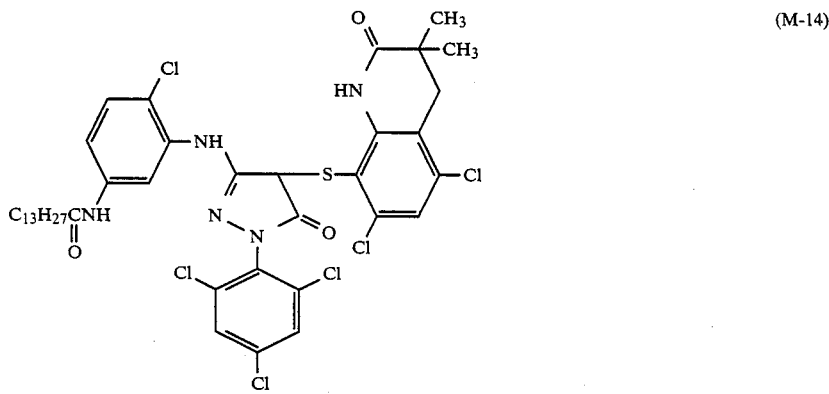
(M-14)
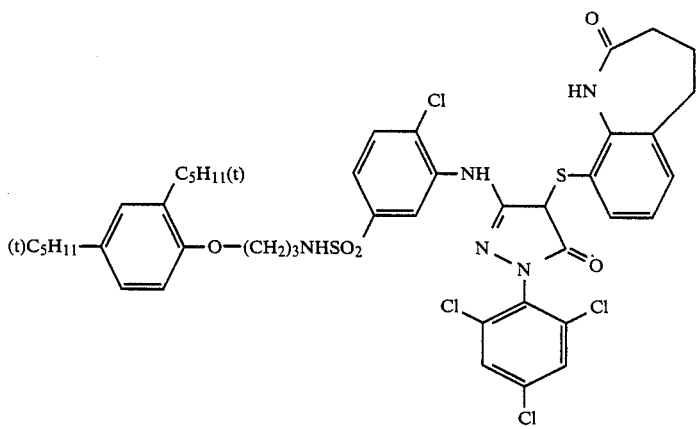
(M-15)

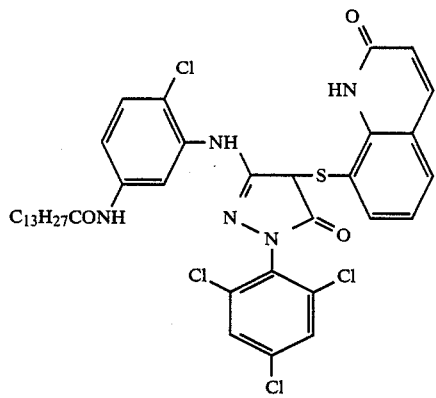
(M-16)
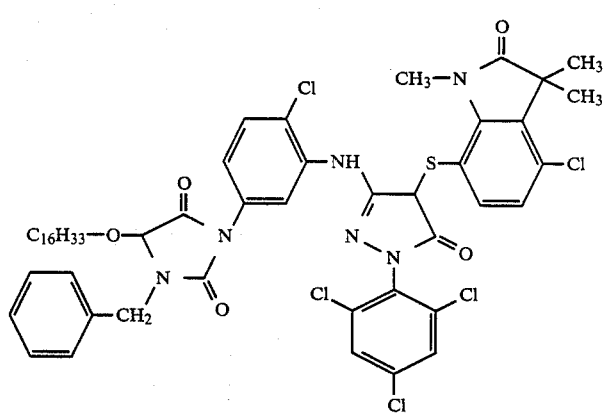
(M-17)
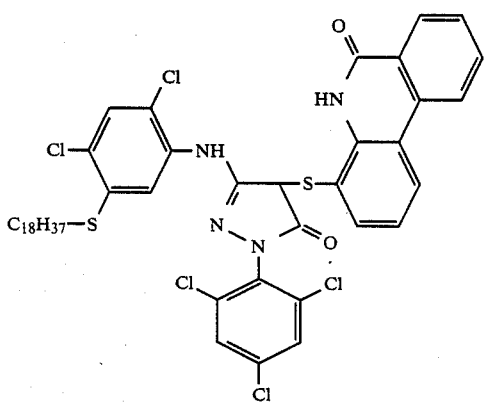
(M-18)
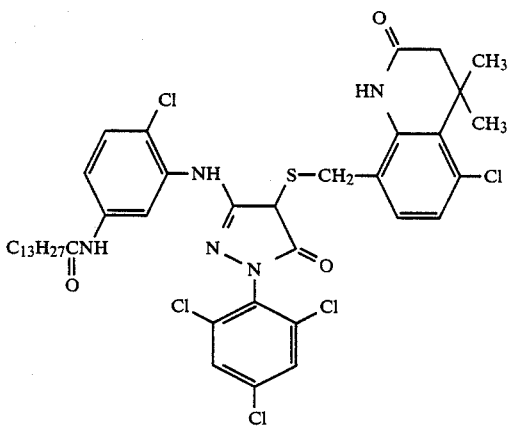
(M-19)

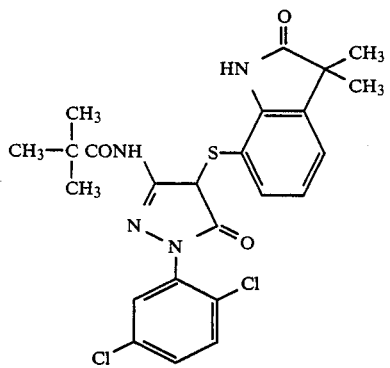
(M-20)
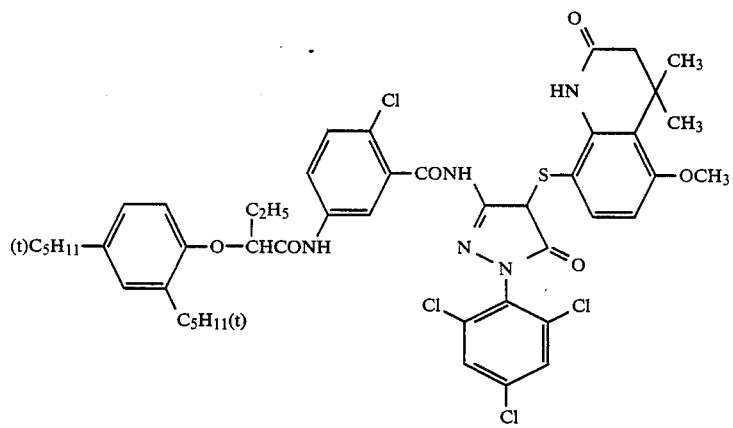
(M-21)
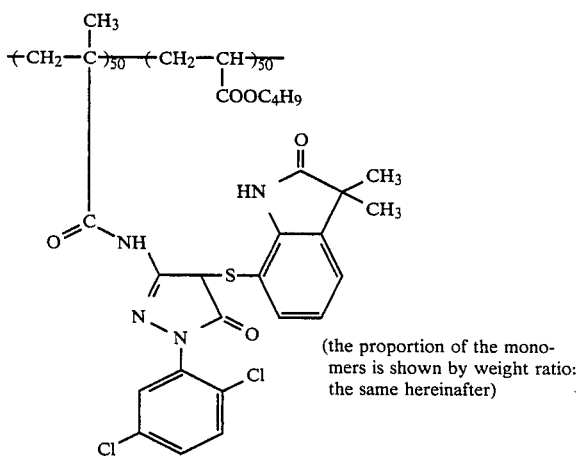
(M-22)
(the proportion of the monomers is shown by weight ratio: the same hereinafter)
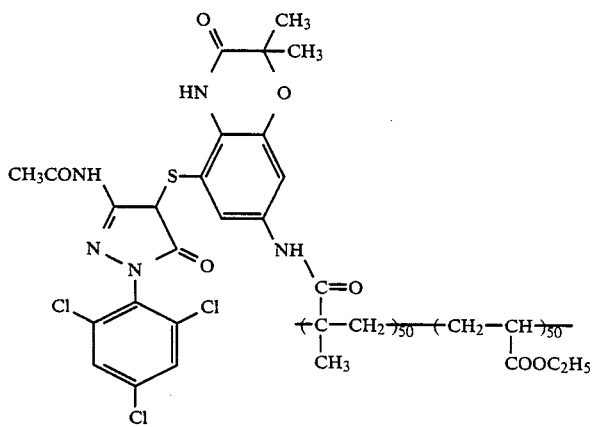
(M-23)

The couplers of the present invention can be easily obtained by allowing four-equivalent pyrazolone mother nuclei to react with a sulfenyl halide prepared by treating in advance the di-sulfide of a mercapto compound with chlorine gas, bromine, or sulfuryl chloride. In the conversion process from a disulfide into a sulfenyl chloride, methylene chloride, ethylene chloride, chloroform and the like are properly used as a solvent, and the reaction temperature is preferably controlled to be from 0° C. to 50° C. The solvent to be used in the process of introducing a sulfenyl chloride to a four-equivalent pyrazolone mother nucleus is preferably dimethylformamide, dimethylacetamide, pyridine or so on. When a neutral solvent such as ethyl acetate, ethylene chloride, acetonitrile or the like is used as the solvent, the addition of an organic base, such as triethylamine, pyridine, etc., is desirable. A suitable reaction temperature in the above process ranges from 20° C. to 100° C.

A process for the synthesis of the couplers to which an arylthio group, which is particularly preferred as the mercapto type coupling eliminable group that characterizes the present invention, is introduced can be illustrated by the following reaction scheme:

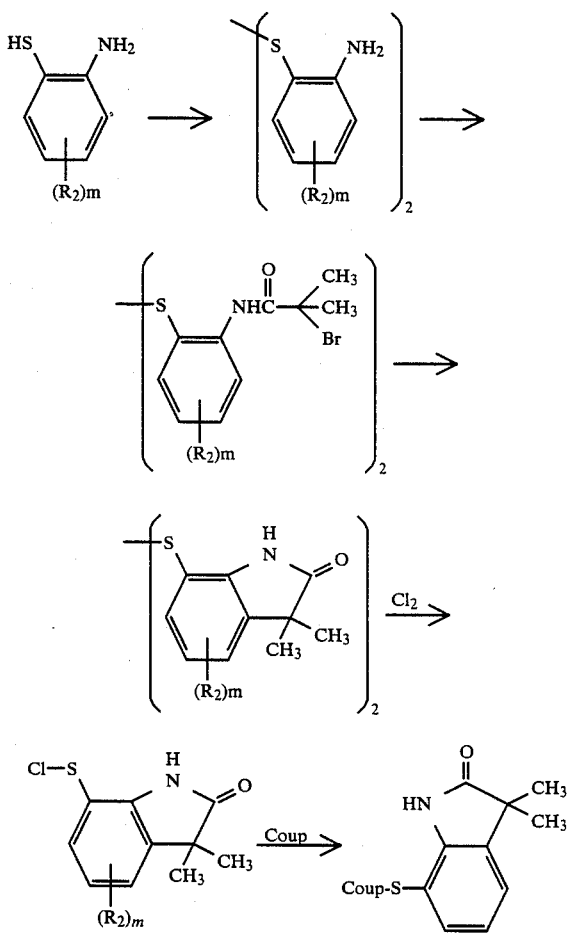

In the above scheme, "Coup" represents a four-equivalent pyrazolone coupler, and Y, $R_2$ and m have the same meanings as defined hereinbefore, respectively.

The step of forming a lactam ring through a ring closure reaction utilizing $AlCl_3$ or the like corresponds to the Friedel-Crafts type acylation reaction as described in ordinary textbooks on organic chemistry.

SYNTHESIS EXAMPLE 1

Synthesis of Coupler (M-1)

In a stream of nitrogen, 12.4 g of bis(2-aminophenyl)-disulfide was added to 100 ml of acetonitrile, and further added thereto was 18.6 g of α-bromo-α-methylpropionic acid chloride. The resulting mixture was heated under reflux for 3 hours. After removal of acetonitrile, 100 ml of ethylene chloride was added to the reaction product, and gradually added thereto was 28 g of anhydrous aluminium chloride at room temperature. After the conclusion of the additional materials, the mixture was heated for 2 hours at 40° C. with vigorous stirring. The reaction mixture was poured into 200 g of ice-cold water containing concentrated hydrochloric acid in order to decompose the aluminium chloride. After the decomposition, 100 ml of chloroform was added to the reaction mixture, and the organic phase was washed with saturated sodium chloride solution three times. The chloroform-ethylene chloride phase was removed, and concentrated to dryness. The product was purified by column chromatography on silica gel to obtain 10.6 g of bis(2-oxo-3,3-di-methyl-7-indolinyl)disulfide.

10.6 g of the thus obtained disulfide was dissolved in 50 ml of chloroform, and 3.7 g of sulfuryl chloride was added thereto at room temperature, followed by 30 minutes of stirring. Then, the chloroform was removed under reduced pressure, and the remaining sulfenyl chloride was added at a time to a solution of 33.8 g of 1-(2,4,6-trichlorophenyl)-3-(2-chloro-5-tetradecanamidoanilino)-5-pyrazolone in 150 ml of dimethylformamide. The temperature of the reaction system was gradually raised to 80° C., and the stirring was continued for 3 hours at that temperature. Then, the reaction mixture was cooled, and 200 ml of ethyl acetate was added thereto. The resulting solution was washed with a saturated solution of sodium chloride three times, and the product produced therefrom was isolated by chromatography on silica gel. Thus, the intended coupler (M-1) was obtained in a yield of 37.7 g.

Elemental Analysis: Anal. calcd.: H, 5.63%; C, 58.14%; N, 8.69%. Found H, 5.64%; C, 58.13%; N, 8.67%.

These couplers are preferably added to a hydrophilic colloid layer in an amount of $1 \times 10^{-3}$ to 1 mole per 1 mole of silver halide present in the same layer or an adjacent layer.

The light-sensitive material of the present invention is described below in further detail.

In the color light-sensitive material of the present invention, it is preferred that a blue-sensitive silver halide emulsion layer, a green-sensitive silver halide emulsion layer and a red-sensitive silver halide emulsion layer is coated on a support in the order described, or alternatively in an arbitrary order.

The type of silver halide usable in the present invention include silver chloride, silver bromide, silver chlorobromide, silver chloroiodobromide, and silver iodobromide. Among them, silver chloride, silver chlorobromide, and silver chloroiodobromide are particularly preferred. Moreover, the preferred halide composition of the silver halide grains contained in one emulsion layer is silver chloride or silver chlorobromide containing silver chloride in a fraction of 90 mol% or more, and substantially not containing any silver iodide. The expression "substantially not containing any silver iodide" signifies a silver iodide content of 1.0 mol% or less. Particularly preferable halide compositions of the silver halide grains are silver chloride and silver chlorobromide having a chloride content of 95 mol% or more, and not containing silver iodide in a substantial sense.

More specifically, the desirable silver halide grains in the present invention are those having a silver bromide-localized phase, and the silver bromide present in the localized phase comprises from more than 10 mol% to less than 70 mol%. Such a silver bromide-localized phase may be located at any part of the grain according to the intended purpose. That is, it may be located at the interior of the grain, or at the surface or the sub-surface portion of the grain. Further, the localized phase may be separately present at the interior and the surface or the sub-surface parts. Moreover, the localized phase may be present at the interior or the surface in a stratiform so as to encircle the silver halide grain, or in a discrete, isolated form. As one example of the preferred forms of the silver bromide-localized phase, mention may be made of such a form that at least 10 mol%, more preferably greter than a 20 mol% portion of the silver bromide attains a local epitaxial growth at the surface of the silver halide grain (especially at the grain edges) to produce a localized phase.

Although a preferred fraction of silver bromide in the localized phase is more than 20 mol%, excessively high fractions thereof tend to give undesirable characteristics to the photographic materials. For example, desensitization is apt to be caused by the pressure applied to the photographic materials, and great changes in sensitivity and gradation occur due to the fluctuation in the compositions of the processing solutions. Taking into account these points, a fraction of the silver bromide in the localized phase preferably ranges from 20 to 60 mol%, particularly from 30 to 50 mol%. Another silver halide which comprises the localized phase is preferably silver chloride. The fraction of silver bromide in the localized phase can be determined by X-ray diffractometry (as described, e.g., in "Shin-Jikkenkagaku Kōza VI Kōzō Kaiseki" compiled by the Japanese Chemical Society and published by Maruzen), the XPS method (as described, e.g., in "Hyōmen Bunseki-IMA, Auger Denshi Kōdenshi Bunkō no Ōyō-" published by Kodansha), or so on. It is desirable that the fraction of the silver present in the localized phase should be from 0.1 to 20%, preferably from 0.5 to 7%, of the whole silver comprising the silver halide grain of the present invention.

At the interface between the above-described silver bromide-localized phase and another phase, there may be a definitive phase boundary, or a short transition range wherein a halogen composition varies by a slow degree. In order to ascertain the location of the silver bromide-localized phase, observations under a microscope or application of the method described in EP-A2-0273430 are effective.

Various kinds of processes can be employed for forming such a silver bromide-localized phase. For instance, the localized phase can be formed by reacting soluble silver salts with soluble halides in accordance with a single jet process or a double jet process. In addition, the localized phase can be formed using a so-called conversion process which includes the step of converting the already formed silver halide into one which has a smaller solubility product. Moreover, the localized phase can be formed through the addition of fine grains of silver bromide and the recrystallization thereof at the grain surface of the silver chloride.

These preparation processes are described, for example, in the above-cited EP-A2-0273430.

It is desirable for enhancing the effects of the present invention that metal ions other than the silver ion (e.g., Group VIII metal ions, Group II (of the Periodic Table) transition metal ions, lead ion, thallium ion) or complex ions of such metals should be incorporated in the localized phase or the substrate of the silver halide grains of the present invention.

In the localized phase, iridium ion, rhodium ion, iron ion and the like can be mainly used, while in the substrate metal ions selected from among osmium, iridium, rhodium, platinum, ruthenium, palladium, cobalt, nickel, iron and the like ions, or complex ions of such metals can be mainly used in combination. In addition, these metal ions can be used in both the localized phase and the substrate, provided that they differ in kind and in the concentration between the localized phase and the substrate.

Incorporation of metal ions into the localized phase and/or another part (substrate) of the silver halide grain can be achieved by the addition of these metals to solutions for preparing a silver halide emulsion prior to grain formation, or in the course of grain formation or physical ripening of the grains. For instance, metal ions can be added to an aqueous solution of gelatin, an aqueous solution of halide, an aqueous solution of silver salt, or other aqueous solutions in forming silver halide grains.

On the other hand, metal ions can be introduced into silver halide grains of a host silver halide emulsion by previously incorporating the metal ions into fine grains of silver halide, and then dissolving the fine grains in the host silver halide emulsion. This process is effective in particular for introducing metal ions into the silver bromide-localized phase present at the surface of silver halide grain. The addition process can be properly changed depending on which location in the silver halide grain the metal ions are intended to be introduced.

In particular, it is desirable that the localized phase should be deposited together with at least a 50% portion of the whole iridium added at the time of the above-described preparation of the silver halide grains.

The expression "the localized phase is deposited together with iridium ion" signifies that an iridium compound is supplied simultaneously with, just prior to, or directly after the supply of silver and/or halogen ions for forming the localized phase.

As for the silver halide grains relating to the present invention, those having any face at the exterior surface, for example, those having (100) face, those having (111) face, those having both (100) and (111) faces, and those comprising higher order faces, are used to an advantage.

Silver halide grains to be used in the present invention may have a regular crystal form, such as that of a cube, tetradecahedron, octahedron, etc., an irregular crystal form, such as that of a sphere, a tabular, etc., or a composite form of these crystal forms. Also, a mixture of grains having different crystal forms can be used. In such a mixture, it is desirable that grains having a regular crystal form should be contained in a fraction of 50% or more, preferably 70% or more, and more preferably 90% or more.

In addition, a silver halide emulsion to be used in this invention may be such an emulsion as to contain tabular grains having an average aspect ratio (diameter/thickness ratio) of 5 or more, particularly 8 or more, in a fraction of 50% or more, based on the projected area of the whole grains.

An average size of the silver halide grains relating to the present invention may be within the conventional range, and preferably from 0.1 to 1.5 microns. The grain size distribution may be polydispersed or monodispersed and is preferably monodispersed in the present invention. A degree of monodispersion in the grain size distribution is preferably 20% or less, preferably 15% or less, expressed in terms of the statistical variation coefficient (a value obtained by dividing the standard deviation S in case of a circular approximation of the projected areas by an average diameter d).

Two or more kinds of tabular grain emulsions as described above, or two or more kinds of monodispersed emulsions as described above may be mixed. When mixing such emulsions, it is desirable that at least one emulsion among them should have a variation coefficient within the above-described range, and more desirably the variation coefficient of the mixed emulsion should be within the above-described range.

A so-called substrate part, other than the localized phase, of the silver halide grains to be used in the present invention may be uniform throughout, or different in composition between a surface portion and an inner portion.

Silver halide emulsions which have been physically ripened, chemically ripened and spectrally sensitized are generally employed in this invention.

Chemical sensitizers used for chemical ripening include those described in JP-A-62-215272 (The term "JP-A" as used herein means an "unexamined published Japanese patent application"), from the lower right column on page 18 to the upper right column on page 22. As for the spectral sensitizers, those described supra, from the upper right column on page 22 to page 38, are preferably used.

As for the antifoggants or the stabilizers to be used during the preparation or upon storage of the silver halide emulsion, those described in the above-cited patent, from page 39 to the upper right column on page 72, can preferably be used in the present invention.

In color photographic materials, yellow couplers, magenta couplers and cyan couplers, which produce yellow, magenta and cyan colors, respectively, by coupling with the oxidation product of an aromatic amine type color developer, are generally used.

Among the yellow couplers which can be used in this invention, acylacetamide derivatives such as benzoylacetanilides and pivaloylacetanilides are preferred over the others.

In particular, yellow couplers represented by the following general formulae (Y-1) and (Y-2) are used to a great advantage:

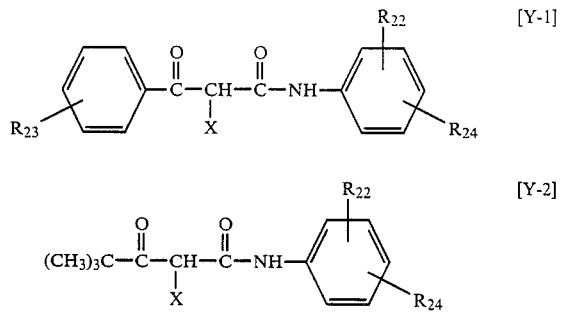

wherein X represents a hydrogen atom, or a coupling eliminable group; $R_{24}$ represents a nondiffusible group containing 8 to 32 carbon atoms; $R_{22}$ represents a hydrogen atom, or at least one halogen atom, lower alkyl group (preferably $C_{1-4}$), lower alkoxy group (preferably $C_{1-4}$) or nondiffusible group containing 8 to 32 carbon atoms; and $R_{23}$ represents a hydrogen atom or at least one substituent group, and when $R_{23}$ represents plural substituent groups they may be the same or different.

Details of the pivaloylacetanilide type yellow couplers are described in U.S. Pat. No. 4,622,287, from line 15 in column 3 to line 39 in column 8, and U.S. Pat. No. 4,623,616, from line 50 in column 14 to line 41 in column 19.

Details of the benzoylacetanilide type yellow couplers are described, e.g., in U.S. Pat. Nos. 3,408,194, 3,933,501, 4,046,575, 4,135,958, and 4,401,752.

Representative examples of the pivaloylacetanilide type yellow couplers include the Examples from (Y-1) to Y-39) disclosed in the above-cited U.S. Pat. No. 4,622,287, from column 37 to column 54. In particular, (Y-1), (Y-4), (Y-6), (Y-7), (Y-15), (Y-21), (Y-22), (Y-23), (Y-26), (Y-35), (Y-36), (Y-37), (Y-38) and (Y-39) are preferably employed in the present invention.

In addition, Compound Examples from (Y-1) to (Y-33) disclosed in the above-cited U.S. Pat. No. 4,623,616 can be utilized. In particular, (Y-2), (Y-7), (Y-8), (Y-12), (Y-20), (Y-21), (Y-23) and (Y-29) are preferred in the present invention.

Other representative examples which can be preferably used in the present invention include Compound Example (34) disclosed in U.S. Pat. No. 3,408,194, column 6; Compound Examples (16) and (19) disclosed in U.S. Pat. No. 3,933,501, column 8; Compound Example (9) disclosed in U.S. Pat. No. 4,046,575, columns 7-8; Compound Example (1) disclosed in U.S. Pat. No. 4,133,958, columns 5-6; Compound Example 1 disclosed in U.S. Pat. No. 4,401,752, column 5; and the compounds from (a) to (h) illustrated below:

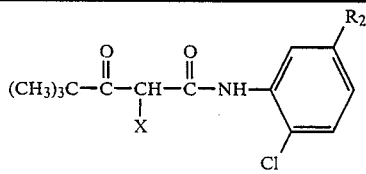

| Compound Example | R₂₂ | X |
|---|---|---|
| a | —COOCH(CH₃)COOC₁₂H₂₅ | (triazolidinedione with N-phenyl and N-CH₂-phenyl) |
| b | —COOCH(C₄H₉)COOC₁₂H₂₅ | " |
| c | —NHCO(CH₂)₃O—(3,5-di-t-C₅H₁₁-phenyl) | —O—C₆H₄—SO₂—C₆H₄—OCH₂—phenyl |
| d | " | (thiadiazole =NSO₂-p-tolyl with isopropyl) |
| e | " | C₆H₁₃OCO—CH(imidazolyl) |
| f | —NHSO₂C₁₂H₂₅ | —O—C₆H₄—COOCH(CH₃)₂ |
| g | —NHSO₂C₁₆H₃₃ | (triazine with morpholino) |
| h | —NHCOCH(CH₃)CH₂SO₂C₁₂H₂₅ | (hydantoin with N-CH₂-phenyl) |

Of the above-cited couplers, those containing a nitrogen atom as the coupling eliminable atom are particularly preferred.

Suitable examples of other magenta couplers which can be used together with the pyrazolone type magenta couplers of the present invention include those of the oil-protected indazolone or the cyanoacetyl types, more preferably those of the 5-pyrazolone type and those of the pyrazoloazole types, such as pyrazolotriazoles. As for the 5-pyrazolone type couplers, those having an arylamino group or an acylamino group at the 3-position are advantageous from the standpoint of hue and density of the developed colors, and representative examples thereof are described in U.S. Pat. Nos. 2,311,082, 2,343,703, 2,600,788, 2,908,573, 3,062,653, 3,152,896, 3,939,015, and so on. Suitable examples of coupling eliminable groups of the two-equivalent 5-pyrazolone type couplers include those having an N-eliminable group, as disclosed in U.S. Pat. No. 4,310,619; and the arylthio groups disclosed in U.S. Pat. No. 4,351,897. Also, the high density of the developed color is obtained by the ballast group-containing 5-pyrazolone type couplers disclosed in European Patent 73,636.

Suitable examples of pyrazoloazole type couplers include the pyrazolobenzimidazoles disclosed in U.S. Pat. No. 2,369,879, and preferably the pyrazolo[5,1-c][1,2,4]triazoles disclosed in U.S. Pat. No. 3,725,067, the pyrazolotetrazoles described in *Research Disclosure*, 24220 (June 1984) and the pyrazolopyrazoles described in *Research Disclosure*, 24230 (June 1984). All of the above-described couplers may assume a polymerized form.

More specifically, those compounds described above are represented by the following general formulae (M-I), (M-II) and (M-III), respectively:

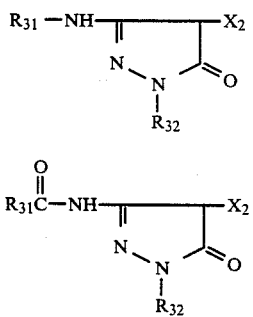

(M-I)

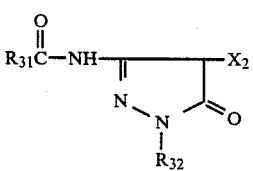

(M-II)

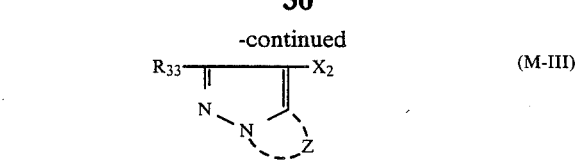

(M-III)

wherein $R_{31}$ represents a nondiffusible group containing 8 to 32 carbon atoms in total; $R_{32}$ represents a phenyl group or a substituted phenyl group; $R_{33}$ represents a hydrogen atom, or a substituent group; Z represents nonmetal atoms necessary to complete a 5-membered azole ring containing 1 to 4 nitrogen atoms, which may have a substituent group (including a group having a condensed ring); $X_2$ represents a hydrogen atom, or a group capable of splitting off.

Details of substituent groups represented by $R_{33}$ and those which the azole ring may have are described, for example, in U.S. Pat. No. 4,540,654, from line 41 in column 2 to line 27 in column 8.

Pyrazoloazole type couplers having favorable properties with respect to a low amount of side absorption in the yellow region and a high fastness to light include imidazo[1,2-b]pyrazoles disclosed in U.S. Pat. No. 4,500,630. Those pyrazoloazole type couplers which are particularly preferred over the others with respect to the above-described properties include the pyrazolo[1,5-b][1,2,4]triazoles disclosed in U.S. Pat. No. 4,540,654.

Examples of other favorable pyrazoloazole type couplers include pyrazolotriazole couplers having a branched alkyl group attached directly to the 2-, 3- or 6-position of the pyrazolotriazole ring, as disclosed in JP-A-61-65245; pyrazoloazole couplers containing a sulfonamido group in a molecule, as disclosed in JP-A-61-65246; pyrazoloazole couplers containing an alkoxyphenylsulfonamido group as a ballast group, as disclosed in JP-A-61-147254; and pyrazolotriazole couplers having an alkoxy group or an aryloxy group at the 6-position, as disclosed in European Patent (unexamined published) 226,849.

Specific examples of the above-described couplers are illustrated below:

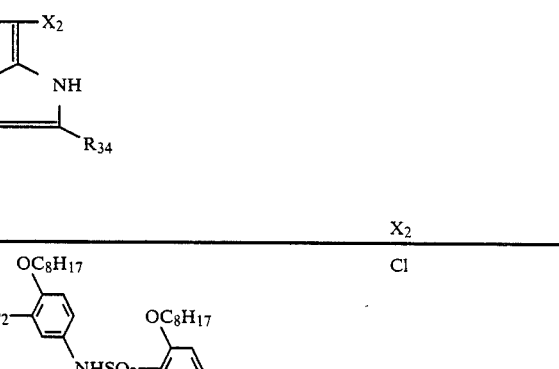

| Compound | $R_{33}$ | $R_{34}$ | $X_2$ |
|---|---|---|---|
| $M_1$-1 | $CH_3-$ | 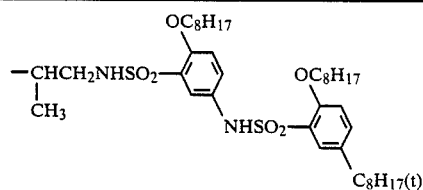 | Cl |
| $M_1$-2 | " | 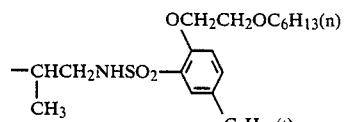 | " |

-continued

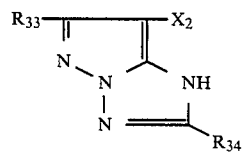

| Compound | $R_{33}$ | $R_{34}$ | $X_2$ |
|---|---|---|---|
| $M_1$-3 | " | -CHCH₂NHSO₂-[2-OC₈H₁₇, 5-C₈H₁₇ phenyl]  (CH₃ branch) | -O-[4-CH₃ phenyl] |
| $M_1$-4 | 2-OCH₃ phenoxy | [3-CH₃ phenyl]-NHSO₂-[2-OC₈H₁₇, 5-C₈H₁₇(t) phenyl] | -S-[2-OC₄H₉, 5-C₈H₁₇(t) phenyl] |
| $M_1$-5 | CH₃- | -CHCH₂NHSO₂-[2-OC₂H₄OC₂H₅, 5-NHSO₂-(2-OC₈H₁₇, 5-C₈H₁₇(t) phenyl) phenyl]  (CH₃ branch) | Cl |
| $M_1$-6 | " | -CCH₂NHSO₂-[2-OC₈H₁₇, 5-NHSO₂-(2-OC₈H₁₇, 5-C₈H₁₇(t) phenyl) phenyl]  ((CH₃)₂ branches) | " |
| $M_1$-7 | phenyl-OCH₂CH₂O- | -CH₂CH₂NHSO₂-[2-(4-OCH₃ phenoxy), 5-NHSO₂-(2-OC₈H₁₇, 5-C₈H₁₇(t) phenyl) phenyl] | -S-[2-OC₄H₉, 5-C₈H₁₇(t) phenyl] |
| $M_1$-8 | CH₂CH₂O- | " | " |
| $M_1$-9 | [2-OC₈H₁₇, 5-C₈H₁₇(t) phenyl]-SO₂NH-[phenyl]-O(CH₂)₂O- | 3,4-diCl phenyl | -S-[2-OC₄H₉, 5-C₈H₁₇(t) phenyl] |
| $M_1$-10 | 2-OCH₃ phenoxy | -CHCH₂NHSO₂-[2-OC₈H₁₇(n), 5-C₈H₁₇(t) phenyl]  (CH₃ branch) | Cl |
| $M_1$-11 | CH₃- | HO-[phenyl]-SO₂-[phenyl]-OCHCONH-[phenyl]-(CH₂)₃  (C₁₀H₂₁ branch) | Cl |
| $M_1$-12 | " | (n)C₆H₁₃-CHCH₂SO₂-(CH₂)₂-  ((n)C₈H₁₇ branch) | " |

-continued

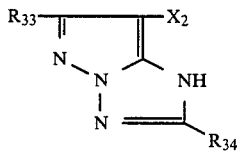

| Compound | $R_{33}$ | $R_{34}$ | $X_2$ |
|---|---|---|---|
| $M_1$-13 | $\begin{array}{c}CH_3\\\phantom{X}\diagdown\\\phantom{XX}CH-\\\phantom{X}\diagup\\CH_3\end{array}$ | 2-$OC_8H_{17}$, 5-$C_8H_{17}(t)$-phenyl-$SO_2$-$(CH_2)_3$- | " |
| $M_1$-14 | $+CH-CH_2\rangle_{50}+CH_2-C\rangle_{50}-$ <br> $\phantom{XX}|$ $\phantom{XXXXXXXXX}|$ <br> $COOCH_2CH_2OCH_3\phantom{X}CONH-$ with $CH_3$ on quaternary C | $CH_3-CH-$ <br> $\phantom{XXX}|$ <br> $\phantom{XX}CH_2NHSO_2CH_3$ | " |
| $M_1$-15 | phenyl-O- | 2-$O_8H_{17}$, 5-$C_8H_{17}(t)$-phenyl with $(CH_2)_2NHSO_2-$ | Cl |
| $M_1$-16 | 3-Cl-phenyl-O- | 2-$O_8H_{17}$, 5-$C_8H_{17}(t)$-phenyl with $(CH_2)_2NHSO_2-$ | 2-$OC_4H_9$, 5-$C_8H_{17}(t)$-phenyl-S- |

(the proportion of monomers is shown by weight ratio)

Representative cyan couplers include those of the phenol type and those of naphthol type.

Suitable examples of the phenol type cyan couplers include those having an acylamino group and an alkyl group at the 2- and the 5-positions of the phenol nucleus, respectively, in which the polymeric couplers are included, as disclosed in U.S. Pat. Nos. 2,369,929, 4,518,687, 4,511,647, 3,772,002, and so on. Typical representative examples of such couplers include the coupler used in Example 2 of Canadian Patent 625,822, Compound (1) disclosed in U.S. Pat. No. 3,772,002, Compounds (I-4) and (I-5) disclosed in U.S. Pat. No. 4,564,590, Compounds (1), (2), (3) and (24) disclosed in JP-A-61-39045, and Compound (C-2) disclosed in JP-A-62-70846.

Other examples of the phenol type cyan couplers include the 2,4-diacylaminophenol type couplers disclosed in U.S. Pat. Nos. 2,772,162, 2,895,826, 4,334,011 and 4,500,653, and JP-A-59-164555. Typical representative couplers include Compound (V) disclosed in U.S. Pat. No. 2,895,826, Compound (17) disclosed in U.S. Pat. No. 4,557,999, Compounds (2) and (12) disclosed in U.S. Pat. No. 4,565,777, Compound (4) disclosed in U.S. Pat. No. 4,124,396, and Compound (I-19) disclosed in U.S. Pat. No. 4,613,564.

Additional examples of the phenol type cyan couplers include the condensed-ring compounds formed by condensing phenol nuclei and nitrogen-containing hetero rings, as disclosed in U.S. Pat. Nos. 4,327,173, 4,564,586 and 4,430,423, JP-A-61-390441, and JP-A-61-100222. Typical representative examples of such couplers are Couplers (1) and (3) disclosed in U.S. Pat. No. 4,327,173, Compounds (3) and (16) disclosed in U.S. Pat. No. 4,564,586, Compounds (1) and (3) disclosed in U.S. Pat. No. 4,430,423, and the compounds illustrated below:

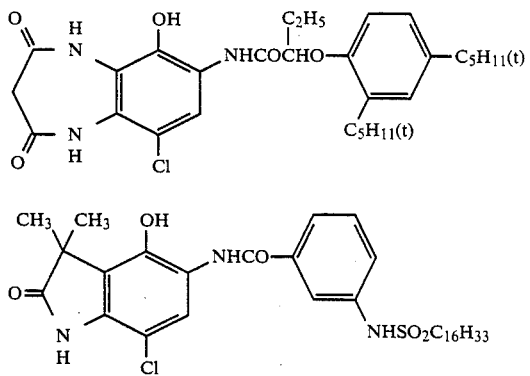

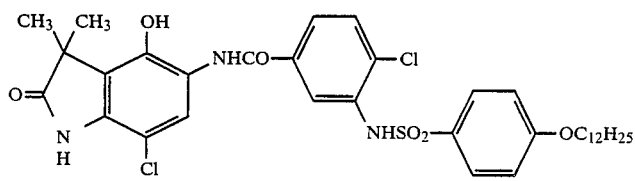
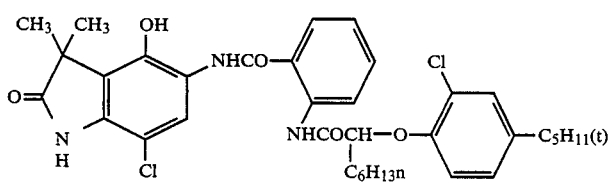
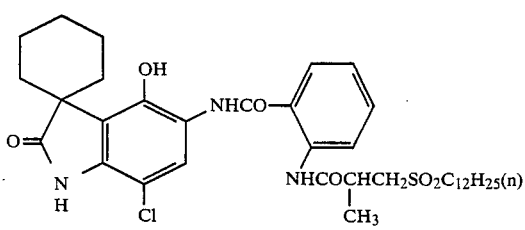
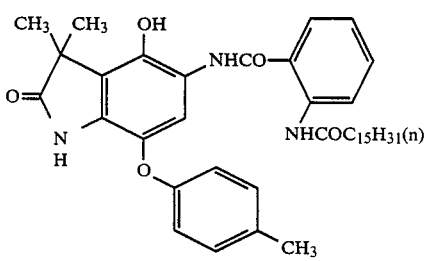
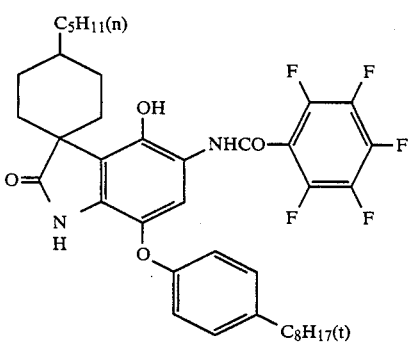
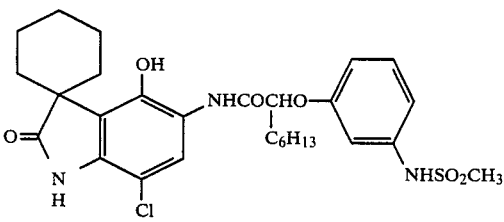
In addition to the cyan couplers of the above-mentioned types, the diphenylimidazole type cyan couplers disclosed in EP-A2-0249453, specific examples of which are illustrated below, can also be employed in the present invention:

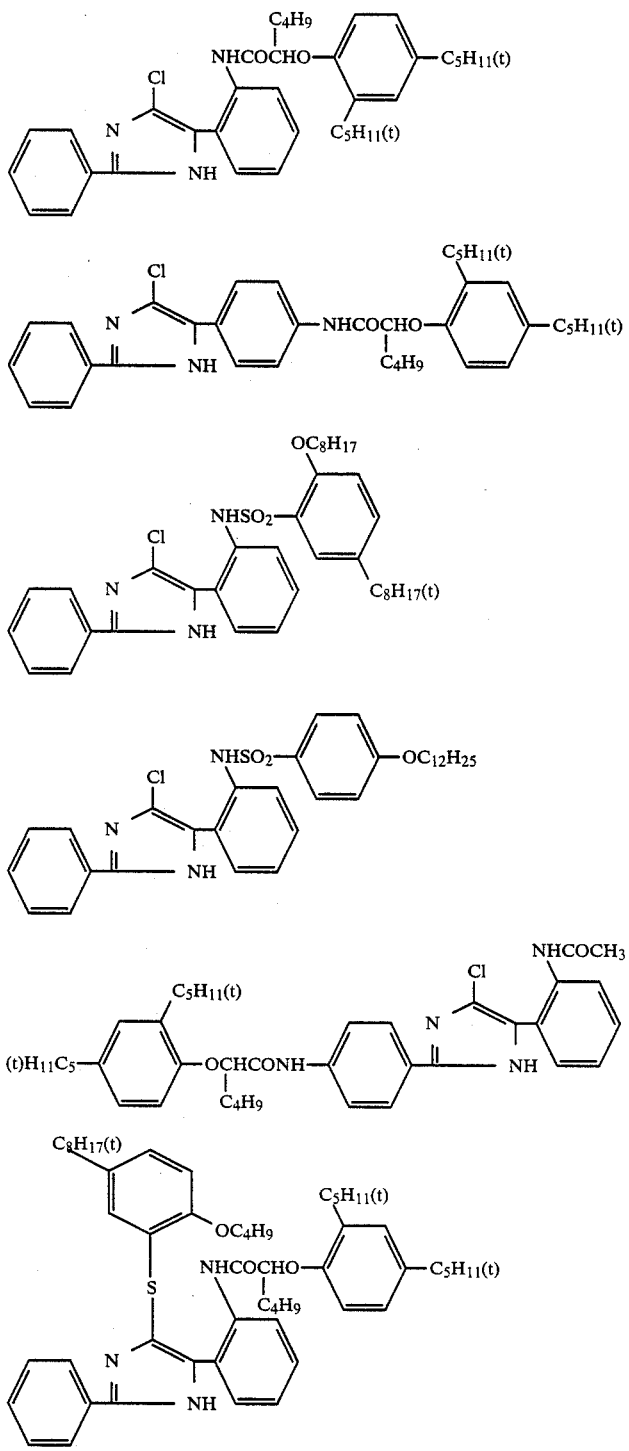

Further, ureido type couplers disclosed in U.S. Pat. Nos. 4,333,999, 4,451,559, 4,444,872, 4,427,767 and 4,579,813, and EP-B1-067689 can be employed as the phenol type cyan coupler. Typical representative examples of such couplers are Coupler (7) disclosed in U.S. Pat. No. 4,333,999, Coupler (1) disclosed in U.S. Pat. No. 4,451,559, Coupler (14) disclosed in U.S. Pat. No. 4,444,872, Coupler (3) disclosed in No. 4,427,767, Couplers (6) and (24) disclosed in U.S. Pat. No. 4,609,619, Couplers (1) and (11) disclosed in U.S. Pat. No. 4,579,813, Couplers (45) and (50) disclosed in EP-B1-067689, Coupler (3) disclosed in JP-A-61-42658, and so on.

As for the naphthol type cyan couplers, those having an N-alkyl-N-arylcarbamoyl group at the 2-position of their respective naphthol nuclei (as disclosed, e.g., U.S. Pat. No. 2,313,586), those having an alkylcarbamoyl group at the 2-position (as disclosed, e.g., in U.S. Pat. Nos. 2,474,293 and 4,282,312), those having an arylcarbamoyl group at the 2-position (as disclosed, e.g., in JP-B-50-14523), those having a carbon-amido or sulfonamido group at the 2-position (as disclosed, e.g., in JP-A-61-145557, and JP-A-61-153640), those containing an aryloxy group as the splitting-off group (as disclosed, e.g., in U.S. Pat. No. 3,476,563), those containing a substituted alkoxy group as the splitting-off group (as disclosed, e.g., in U.S. Pat. No. 4,296,199), those containing a glycolic acid group as the splitting-off group (as disclosed, e.g., in JP-B-60-39217), and so on can be used in the present invention.

These couplers can be incorporated in an emulsion layer so that they are dispersed together with at least one high boiling organic solvent. High boiling organic solvents which can be preferably used therein are represented by the following general formulae (A) to (E):

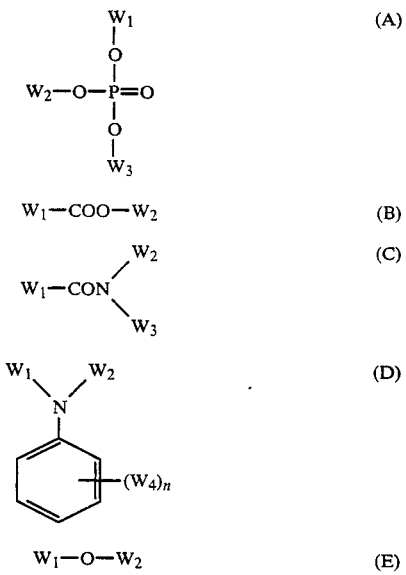

wherein $W_1$, $W_2$ and $W_3$ each represent a substituted or unsubstituted alkyl, cycloalkyl, alkenyl, aryl or heterocyclic group; $W_4$ represents $W_1$, $OW_1$, or $S-W_1$; n represents an integer of 1 to 5, and when n is 2 or more, the $W_4$'s may be the same or different; and in formula (E), a condensed ring may be formed by $W_1$ and $W_2$.

Also, the above-described couplers can be made to sink into loadable latex polymers (as disclosed, e.g., in U.S. Pat. No. 4,203,716) in the presence or absence of the above-illustrated high boiling organic solvents, or dissolved in polymers insoluble in water and soluble in organic solvents, and then dispersed into aqueous solutions of hydrophilic colloids in the form of an emulsion.

As such polymers, homopolymers or copolymers disclosed in International Patent WO88/00723, pages 12 to 30, are preferably used. The use of acrylamide type polymers are particularly preferable from the standpoint of the stabilization of the color images to be formed.

The photographic material produced in accordance with the present invention may contain as a color fog inhibitor a hydroquinone derivative, an aminophenol derivative, a gallic acid derivative, an ascorbic acid derivative, or the like.

Various kinds of discoloration inhibitors can be used in the photographic material of the present invention. Typical examples of organic discoloration inhibitors for cyan, magenta and/or yellow images include hindered phenols represented by hydroquinones, 6-hydroxychromans, 5-hydroxycoumarans, spirochromans, p-alkoxyphenols and bisphenols, gallic acid derivatives, methylenedioxybenzenes, aminophenols, hindered amines, and ether or ester derivatives obtained by silylation or alkylation of phenolic hydroxy groups of the above compounds. Also, metal complex salts represented by (bis-salicylaldoximato)nickel complex and (bis-N,N-dialkyldithiocarbamato)nickel complex can be employed as a discoloration inhibitor.

Specific examples of the organic discoloration inhibitors are described in the patents cited below. That is, those of hydroquinones are disclosed, e.g., in U.S. Pat. Nos. 2,360,290, 2,418,613, 2,700,453, 2,701,197, 2,728,659, 2,732,300, 2,735,765, 3,982,944 and 4,430,425, British Patent 1,363,921, U.S. Pat. Nos. 2,710,801 and 2,816,028, and so on; those of 6-hydroxychromans, 5-hydroxycoumarans and spirochromans are disclosed, e.g., in U.S. Pat. Nos. 3,432,300, 3,573,050, 3,574,627, 3,698,909 and 3,764,337, JP-A-52-152225, and so on; those of spiroindanes are disclosed in U.S. Pat. No. 4,360,589; those of p-alkoxyphenols are disclosed, e.g., in U.S. Pat. No. 2,735,765, British Patent 2,066,975, JP-A-59-10539, JP-B-57-19765 (The term "JP-B" as used herein means an "examined Japanese patent publication"), and so on; those of hindered phenols are disclosed, e.g., in U.S. Pat. No. 3,700,455, JP-A-52-72224, U.S. Pat. No. 4,228,235, JP-B-52-6623, and so on; those of gallic acid derivatives, methylenedioxybenzenes and aminophenols are disclosed, e.g., in U.S. Pat. No. 3,457,079, U.S. Pat. No. 4,332,886 and JP-B-56-21144, respectively; those of hindered amines are disclosed, e.g., in U.S. Pat. Nos. 3,336,135 and 4,268,593, British patents 1,326,889, 1,354,313 and 1,410,846, JP-B-51-1420, JP-A-58-114036, JP-A-59-53846, JP-A-59-78344, and so on; those of ether and ester derivatives of phenolic hydroxy groups are disclosed, e.g., in U.S. Pat. Nos. 4,155,765, 4,174,220, 4,254,216 and 4,264,720, JP-A-54-145530, JP-A-55-6321, JP-A-58-105147, JP-A-59-10539, JP-B-57-37856, U.S. Pat. No. 4,279,990, JP-B-53-3263, and so on; and those of metal complexes are disclosed, e.g., in U.S. Pat. Nos. 4,050,938 and 4,241,155, British Patent 2,027,731(A), and so on. Each of these compounds can be effectively used by being emulsified together with a color coupler corresponding thereto in a proportion of 5 to 100 wt% relative to the color coupler, and then being incorporated into a light-sensitive layer. In order to prevent a cyan dye image from undergoing deterioration by exposure to heat and light, especially light, it is more effecfive to introduce a ultraviolet absorbent into both layers adjacent to the cyan color-producing layer.

Among the above-cited discoloration inhibitors, spiroindanes and hindered amines are particularly preferred.

In the present invention, it is desirable that compounds as described below is used together with the above-described couplers, especially with the pyrazoloazole couplers.

More specifically, for the purpose of preventing the generation of stain and other side reactions attributable to the production of developed dyes by the reaction between couplers and a color developer or the oxidation product thereof remaining in the film upon storage after photographic processing, it is desirable that a compound (F) capable of producing a chemically inert and substantially colorless compound by chemically binding to an aromatic amine developing agent remaining after color development, and/or a compound (G) capable of producing a chemically inert and substantially colorless compound by chemically binding to the oxidation product of an aromatic amine color developing agent remaining after color development are used in combination, or independently.

Compounds preferred as compound (F) include those undergoing a reaction with p-anisidine in such a manner that the rate constant in the second order reaction, k2, should range from 1.0 l/mol sec to $1 \times 10^{-5}$ l/mol.sec (in 80° C. trioctyl phosphate).

When k2 is greater than the above-defined range, the compounds themselves are unstable, and it frequently happens that they decompose by the reacttion with gelatin or water. On the other hand, when k2 is smaller than the above-defined range, the reaction with the residual aromatic amine developing agent is slow, and as a result of such a slow reaction, it frequently happens that the action of this compound, or the prevention of the side reaction of the residual aromatic amine developing agent, cannot be achieved.

Compounds which are more preferable as compound (F) can be represented by the following general formula (FI) or (FII):

$$R1-(A)_n-X \quad \text{[FI]}$$

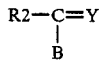

$$R2-C=Y \quad \text{[FII]}$$
$$\quad | \quad$$
$$\quad B \quad$$

wherein R1 and R2 each represent an aliphatic group, an aromatic aryl group, or a heterocyclic group; X is a group which is eliminated by the reaction with aromatic amine developing agents, preferably at a pH of not higher than 8; A is a group which forms a chemical bond by the reaction with the aromatic developing agents; n represents 1 or 0; B represents a hydrogen atom, an aliphatic group, an aromatic group, a heterocyclic group, an aliphatic or aromatic acyl group, or a aliphatic or aromatic sulfonyl group; and Y represents a group capable of accelerating the addition of an aromatic amine developing agent to the compound of general formula (FII); and further, R1 and X, and Y and R2 or B, respectively, may combine with each other to complete a cyclic structure.

The chemical binding to the residual aromatic amine developing agent can be typically effected through a substitution reaction or an addition reaction.

Specific examples of the compounds represented by general formulae (FI) and (FII) are disclosed in Japanese Patent Application Nos. 62-158342, 62-158643, 62-212258, 62-214681, 62-228034 and 62-279843, and so on.

In addition, the details of the various combinations of the above-described compound (G) and compound (F) are described in Japanese Patent Application No. 63-18439.

The photographic material produced in accordance with the present invention may contain an ultraviolet absorbent in a hydrophilic colloid layer. For instance, benzotriazole compounds substituted by an aryl group (as described, e.g., in U.S. Pat. No. 3,533,794), 4-thiazolidone compounds (as described, e.g., in U.S. Pat. Nos. 3,314,794 and 3,352,681), benzophenone compounds (as described, e.g., in JP-A-46-2784), cinnamic acid esters (as described, e.g., in U.S. Pat. Nos. 3,705,805 and 3,707,375), butadiene compounds (as described, e.g., in U.S. Pat. No. 4,045,229), or benzoxidol compounds (as described, e.g., in U.S. Pat. No. 3,700,455) can be used. Also, ultraviolet absorbing couplers (e.g., cyan dye forming couplers of α-naphthol type) and ultraviolet absorbing polymers may be used. These ultraviolet absorbents may be mordanted in a particular layer.

The photographic material produced in accordance with the present invention may contain water-soluble dyes in the hydrophilic colloid layers as a filter dye, or as that for the prevention of irradiation or for other various purposes. Suitable examples of such dyes include oxonol dyes, hemioxonol dyes, styryl dyes, merocyanine dyes, cyanine dyes and azo dyes. Of these dyes, oxonol dyes, hemioxonol dyes and merocyanine dyes are preferred.

Gelatin is advantageously used as a binder or a protective colloid for the emulsion layers of the photographic material of the present invention. Also, hydrophilic colloids other than gelatin can be used alone or together with gelatin.

The gelatin used in the present invention may be either a lime-processed or an acid-processed one. Details of the preparation of gelatin are described in Arther Veis, *The Macromolecular Chemistry of Gelatin*, Academic Press (1964).

The type of support materials which can be used in the present invention include transparent supports generally used in photographic light-sensitive materials, such as cellulose nitrate film and polyethylene terephthalate film, and reflecting supports. For the object of the present invention to be obtained, reflecting supports are more desirable.

The term "reflecting support" as used in the present invention refers to one which can enhance the reflectivity to contribute to the clarification of the dye images formed in the silver halide emulsion layers, and includes supporting materials on which hydrophobic resins containing light-reflecting substances, such as titanium oxide, zinc oxide, calcium carbonate, calcium sulfate, etc., in a dispersed condition are coated, and films of hydrophobic resins in which light-reflecting substances are dispersed. Specific examples thereof include baryta paper, polyethylene-coated paper, synthetic paper of the polypropylene type, and a reflecting layer-laminated or reflecting substance-containing transparent supports. Suitable examples of such transparent supports include a glass plate, films of polyesters such as polyethylene terephthalate, cellulose triacetate, cellulose nitrate, etc., polyamide films, polycarbonate films, polystyrene films, vinyl chloride resin films, and so on. The support to be used can be properly chosen from the above-cited materials depending on the end-use purpose of the photographic material of the present invention.

As for the light-reflecting substances to be used, it is desirable that white pigments should be thoroughly kneaded in the presence of a surfactant. Pigment grains wherein the surfaces thereof have been treated with a di- to tetra-hydric alcohol are preferably used.

An occupied area rate (%) of fine-grained white pigment per specified unit area can be determined most typically by dividing the observed area into neighbouring unit areas of 6 $\mu$m $\times$ 6 $\mu$m, and measuring an occupied area rate Ri (%) of fine grains projected on each unit area. A variation coefficient of the occupied area rate (%) can be defined as a ratio of the standard deviation of Ri, represented by s, to the mean of Ri, represented by $\bar{R}$. The number of unit areas to be examined as the subject, represented by n, is preferably 6 or more.

Accordingly, the variation coefficient $s/\bar{R}$ can be determined according to the equation, $$s/\bar{R} = \sqrt{\frac{\sum_{i=1}^{n}(Ri - \bar{R})^2}{n-1}} \Big/ \frac{\sum_{i=1}^{n} Ri}{n}$$

In the present invention, a variation coefficient of the occupied area rate (%) of fine-grained pigment is preferably 0.15 or less, particularly preferably 0.12 or less. When the variation coefficient is 0.08 or less, a dispersed condition of the grains can be said to be "uniform" in a substantial sense.

The color photographic light-sensitive material of the present invention is preferably subjected to color development, bleach-fix, and washing (or stabilization) processing steps. Bleach and fixation, on the other hand, need not be carried out in a single bath, but may be carried out with separate baths.

When the photographic processing is carried out continuously, it is desirable in order to save resources and to reduce environmental pollution that the developer should be replenished in a small quantity.

The amount of the color developer to be replenished is preferably 200 ml or less, more preferably 120 ml or less, particularly preferably 100 ml or less, per square meter of the photographic materials processed. The term "amount to be replenished" as used herein is intended to include only an amount of a so-called replenisher for the color developer, but not to include the amount of additives used for supplementing the developer components lost with the lapse of time due to deterioration and concentration. The term additives as used herein is intended to include, for example, water for diluting the concentrated developer, preservatives subject to deterioration with the lapse of time, or alkali agents for elevating pH, and so on.

A color developer to be applied to the present invention is preferably an alkaline aqueous solution containing an aromaic primary amine color developing agent as a main component. As for the color developing agent, p-phenylenediamine compounds are preferably used, though aminophenol compounds also are useful. Typical examples of p-phenylenediamine type color developing agents include 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, 3-methyl-4-amino-N-ethyl-N-β-methoxyethylaniline, and the sulfates, hydrochlorides or p-toluenesulfonates of the above-cited anilines. These compounds may be used as a mixture of two or more thereof, if desired.

Further, the color developer generally contains pH buffering agents, such as carbonates, borates or phosphates of alkali metals, and development inhibitors or antifoggants, such as bromides, iodides, benzimidazoles, benzothiazoles or mercapto compounds. Furthermore, the color developer may optionally contain various kinds of preservatives, such as hydroxylamine, diethylhydroxylamine, sulfites, hydrazines, phenylsemicarbazides, triethanolamine, catechol sulfonic acids, and triethylenediamine(1,4-diazabicyclo[2,2,2]octane)'s; organic solvents, such as ethylene glycol or diethylene glycol; development accelerators such as benzyl alcohol, polyethylene glycol, quaternary ammonium salts or amines; dye-forming couplers; competing couplers; fogging agents such as sodium boronhydride; auxiliary developers such as 1-phenyl-3-pyrazolidone; viscosity imparting agents; and various chelating agents such as aminopolycarboxylic acids, aminopolyphosphonic acids, alkylphosphonic acids and phosphonocarboxylic acids, with typical representatives including ethylenediaminetetraacetic acid, nitrilotriacetic acid, diethylenetriaminepentaacetic acid, cyclohexanediaminetetraacetic acid, hydroxyethylimidinoacetic acid, 1-hydroxyethylidene-1,1-diphosphonic acid, nitrolo-N,N,N-trimethylenephosphonic acid, ethylenediamine-N,N,N',N'-tetramethylenephosphonic acid, ethylenediamine-di(o-hydroxyphenylacetic acid) and salts of these acids.

In carrying out a reversal process, black and white development is generally performed prior to color development. A black and white developer usable therein contains known black and white developing agents, such as dihydroxybenzenes (e.g., hydroquinone), 3-pyrazolidones (e.g., 1-phenyl-3-pyrazolidone) or aminophenols (e.g., N-methyl-p-aminophenol), individually or in combination.

The color developer and the black-and-white developer described above are, in general, adjusted to pH 9-12. These developers are generally replenished in an amount of 3 liter or less per square meter of color photographic material processed, though the replenishing amount depends on the kind of color photographic material processed. When a replenisher containing bromide ion in a reduced concentration is used, the amount of the replenisher can be decreased to 500 ml or less per square meter of the color photographic material processed. When replenishers are used in reduced amounts, it is desired that vaporization and air oxidation should be prevented from occurring in the developers by minimizing the contact area between the processing solutions and air. Also, the amounts of the developers to be replenished can be reduced by adopting means for suppressing the accumulation of bromide ion therein.

After the color development, the photographic emulsion layers are, in general, subjected to a bleach processing step. The bleach processing step may be carried out simultaneously with a fixation processing step (a bleach-fix processing step), or separately therefrom. For the purpose of speeding up the photographic processing step, the bleach processing may be succeeded by a bleach-fix processing step. Also, the processing may be performed with two successive bleach-fix baths, or the fixation processing step may be succeeded by the bleach-fix processing step, or the bleach-fix processing step may be succeeded by the bleach processing step, if desired. Examples of bleaching agents which can be used include compounds of polyvalent metals, such as Fe(III), Co(III), Cr(VI), Cu(II), etc.; peroxy acids; quinones; nitro compounds; and so on. More specifically, ferricyanides; dichromates; organic complex salts formed by Fe(III) or Co(III), and aminopolycarboxylic acid, such as ethylenediaminetetraacetic acid, diethylenetriaminepentaacetic acid, cyclohexanediaminetetraacetic acid, methyliminodiacetic acid, 1,3-diaminopropanetetraacetic acid, glycol ether diamine tetraacetic acid, etc., citric acid, tartaric acid, malic acid, or so on; persulfates; hydrobromides; permanganates; nitrobenzenes; and so on can be cited as representative examples of bleaching agents. Among these bleaching agents, aminopolycarbonatoferrate(III) complexes including ethylenediaminetetraacetonatoferrate(III) complex, and persulfates are preferred over the others from the standpoints of rapid processing and the prevention of environmental pollution. In addition, aminopolycarbonatoferrate(III) complexes are particularly useful in not only a bleaching bath, but also in a bleach-fix bath. The pH of the bleaching or bleach-fix which uses an aminopolycarbonatoferrate(III) complex as a bleaching agent generally ranges from 5.5 to 8, but the processing can be performed at a lower pH for the purpose of increasing the processing speed.

In the bleaching bath, the bleach-fix bath and the prebath thereof, bleach accelerators can be used, if needed.

Specific examples of useful bleach accelerators include compounds containing a mercapto group or a disulfide linkage, as described in U.S. Pat. No. 3,893,858, West German Patents 1,290,812 and 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, JP-A-53-28426, *Research Disclosure*, No. 17129 (July 1978), and so on; thiazolidine derivatives described in JP-A-50-140129; thiourea derivatives described in JP-B-45-8506, JP-A-52-20832, JP-A-53-32735, and U.S. Pat. No. 3,706,561; iodides described in West German Patent 1,127,715, and JP-A-58-16235; polyoxyethylene compounds described in West German Patents 996,410 and 2,748,430; polyamine compounds described in JP-B-45-8836; the compounds described in JP-A-49-42434, JP-A-49-59644, JP-A-53-94927, JP-A-54-35727, JP-A-55-26506, and JP-A-58-163940; and bromide ion. Of these bleach accelerators, the compounds containing a mercapto group or a disulfide linkage are preferred with respect to their large acceleration effect. In particular, the compounds described in U.S. Pat. No. 3,893,858, West German Patent 1,290,812, and JP-A-53-95630 are favored over the others. In addition, the compounds described in U.S. Pat. No. 4,552,834 are also effective. These bleach accelerators may be incorporated in the photographic materials. In the bleach-fix step for the color photographic materials for photography, these bleach accelerators are particularly effective.

Examples of fixers which can be used include thiosulfates, thiocyanates, thioether compounds, thioureas, a large amount of iodide, and so on. Of these fixers, thiosulfates are generally used, and the most widely used type of fixer is ammonium thiosulfate. Examples of preservatives suitable for a bleach-fix bath include sulfites, bisulfites, or adducts of carbonyl compounds and bisulfites.

After a desilvering step, the silver halide color photographic material of the present invention is, in general, subjected to a washing step and/or a stabilizing step. The volume of washing water required in the washing step can be variously determined depending on the characteristics of the photographic materials to be processed (e.g., on what kinds of couplers are incorporated therein), end-use purposes of the photographic materials to be processed, the temperature of washing water, the number of the washing tanks (stage number), the method of replenishing the washing water (as to, e.g., whether the water flows in the countercurrent direction, or not), and other various conditions. Of these conditions, the relation between the number of the washing tanks and the volume of washing water in the multistage countercurrent process can be determined according to the methods described in the *Journal of the Society of Motion Picture and Television Engineers*, volume 64, pages 248 to 253 (May 1955).

According to the multistage countercurrent process described in the above-cited literature, the volume of washing water can be sharply decreased. However, the process has disadvantages, for example, in that bacteria will propagate in the tanks because of an increase in an amount of time that the water stays in the tanks. Another disadvantage is that the suspended matter produced from the bacteria sticks to the photographic materials processed in the tanks. In the processing of the color photographic material of the present invention, the method of reducing calcium and magnesium ion concentrations, which is disclosed in JP-A-62-288838, can be employed to great advantage as the means for solving the above-described problem. Further, bactericides may be used such as isothiazolone compounds and thiabendazoles disclosed in JP-A-57-8542, chlorine-containing germicides such as sodium salt of chlorinated isocyanuric acid, and benzotriazoles, as described in Hiroshi Horiguchi *Bohkin Bohbai Zai no Kagaku* (which means "chemistry of antibacteria and antimolds"), *Biseibutsu no Mekkin Sakkin Bohbai Gijutsu* (which means "Arts of sterilizing and pasteurizing microbe, and proofing against mold"), compiled by Eisei Gijutsu Kai, and *Bohkin- and Bohbaizai Jiten* (which means "Thesaurus of antibacteria and antimolds"), compiled by Nippon Bohkin Bohbai Gakkai.

The washing water to be used in the processing of the photographic materials of the present invention is adjusted to pH 4–9, preferably to pH 5–8. The washing temperature and the washing time can be chosen variously depending on the characteristics and the intended use of the photographic materials to be washed, and are generally chosen to be in the range of 20 sec. to 10 min. at 15° to 45° C., preferably 30 sec. to 5 min. at 25° to 40° C.

Also, the photographic materials of the present invention can be processed directly with a stabilizing solution instead of using the above-described washing water. All the known methods, which are described in JP-A-57-8543, JP-A-58-14834 and JP-A-60-220345, can be applied to the stabilization step in the present invention.

In certain cases, the stabilization step is also performed subsequently to the above-described washing step. For instance, a stabilizing bath containing formaldehyde and a surfactant, which is used as the final bath for color photographic materials for photography use, can be cited.

Also to the stabilizing bath, various kinds of chelating agents and antimold agents can be added.

The washing water and/or the stabilizing solution overflowing the processing baths with the replenishing solution thereof can also be reused in other steps such as in the desilvering step.

For the purposes of simplification and accelerating the photographic processing, a color developing agent may be incorporated into the silver halide color photographic material of the present invention. Preferably the color developing agent should be used in the form of precursors of various types. For instance, compounds of the indoaniline type described in U.S. Pat. No. 3,342,597, compounds of a Schiff base type described in U.S. Pat. No. 3,342,599 and *Research Disclosure*, Nos. 14850 and 15159, aldol compounds described in Supra, No. 13924, metal salt complexes described in U.S. Pat. No. 3,719,492, and urethane compounds described in JP-A-53-135628 can be cited.

In the silver halide color photographic materials of the present invention, various 1-phenyl-3-pyrazolidones may each be incorporated therein for the purpose of accelerating color development, if desired. Typical examples of such compounds are described in JP-A-56-64339, JP-A-57-144547, JP-A-115438, and so on.

The temperature of each processing bath used in the present invention ranges from 10° to 50° C. However, the standard temperature is within the range of 33° to 38° C. Temperatures higher than standard ones can be adopted for reducing the processing time by the acceleration of the processing, while those temperatures lower than standard ones allow the achievement of improved image quality and enhanced stability of the processing bath. Moreover, processing which utilizes cobalt intensification or hydrogen peroxide intensification as described in West German Patent 2,226,770 or U.S. Pat. No. 3,674,499 and may be carried out for the purpose of saving silver.

In order to make the silver halide photographic material of the present invention fully achieve its excellent effects, it is desired that it should be processed with a color developer which is substantially free from benzyl alcohol and contains not more than 0.002 mol/l of bromide ion. The development time should also be controlled so that it is not longer than 2 min. and 30 sec.

The expression "substantially free from benzyl alcohol" as used above is intended to include benzyl alcohol content lower than 2 ml, preferably lower than 0.5 ml, per liter of color developer. In the most desirable case, it means that the benzyl alcohol is absolutely not contained in the color developer at all.

The couplers of the present invention can be used together with a bisaryldisulfide of the following general formula (III) as disclosed in JP-A-63-157150 as a discoloration inhibitor for a color image or a yellow stain formation inhibitor, generally in an amount of from 10 to 150 mg/m², preferably from 30 to 120 mg/m². This compound is preferably contained in the emulsion layer containing the 5-pyrazolone coupler of the present invention:

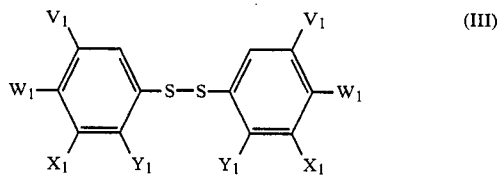

wherein $V_1$, $W_1$, $X_1$ and $Y_1$ each represent a group of the formula $R^{41}$, a nitro group, a halogen atom, a cyano group, a group of the formula $OR^{51}$, a group of the formula $SR^{51}$, a group of the formula $NR^{41}R^{51}$, a group of the formula $COR^{51}$, a group of the formula $COOR^{51}$, a group of the formula $SO_2R^{51}$, a group of the formula $SO_3R^{51}$, a group of the formula $NHCOR^{51}$, a group of the formula $CONR^{41}R^{51}$, a group of the formula $NR^{41}SO_2R^{51}$ or a group of the formula $SO_2NR^{41}R^{51}$, or $X_1$ and $W_1$ each can form a ring by combining with an adjacent substituent group; $R^{51}$ represents a substituted or an unsubstituted alkyl group containing 1 to 20 carbon atoms, a substituted or unsubstituted aryl or cycloalkyl group containing 5 to 20 carbon atoms, or a substituted or an unsubstituted heterocyclic group containing 3 to 10 carbon atoms; and $R^{41}$ represents a hydrogen atom, or the same group as defined as $R^{51}$; but the total number of the carbon atoms contained in all of the substituents $V_1$, $W_1$, $X_1$ and $Y_1$ must be 2 or more, and when two $Y_1$'s are both hydrogen such a compound must be excluded. Two substituents represented by the same symbols may be the same or different.

Among the above-described disulfide compounds, particularly preferred ones are those having $Y_1$ represented by the formula $OR^{51}$ or $NHCOR^{51}$, and those containing $Y_1$ and $X_1$ which combine with each other to complete a ring, as represented by the following general formula (IV):

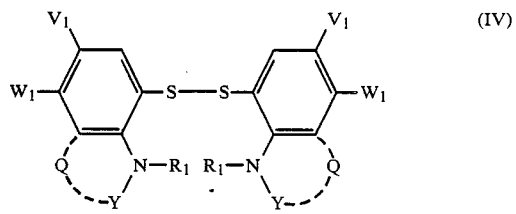

wherein $R_1$, Y and Q have the same meaning as in general formula (I), respectively.

EXAMPLE 1

A paper support laminated with a polyethylene film on both sides thereof, were coated with an emulsion layer and a protective layer as described below in the order given to prepare sample 101.

In a mixture of 20 ml of ethyl acetate and 10 ml of tricresyl phosphate was dissolved 10 g of a magenta coupler (A). The obtained solution was mixed with 300 ml of a 10% aqueous gelatin solution containing 15 ml of 10% sodium dodecylbenzenesulfonate, and coercively stirred to prepare an emulsified dispersion. The resulting dispersion was mixed homogeneously with 600 g of a silver chlorobromide emulsion (containing 0.44 mole of silver, and having an average grain size of 0.4 micron, a cubic grain form with a variation coefficient of 0.09 and a bromide content of 1 mol%), and coated on the support described above at a silver coverage of 0.002 mol/m². A 4% gelatin solution containing sodium tripropylenenaphthylene sulfonate as a coating aid and sodium salt of 1-oxy-s-triazine as a gelatin hardener was coated thereon to a dry thickness of 1 micron.

Samples 102 to 113 were prepared in the same manner as sample 101, except the couplers set forth in Table 1 were used in place of magenta coupler (A), respectively.

The above-described light-sensitive materials were each exposed to light through an optical wedge, and subjected to the photographic processing steps as follows:

| Processing Step | Temperature (°C.) | Time |
|---|---|---|
| Color Development | 35 | 45 sec. |
| Bleach-Fix | 30 to 36 | 45 sec. |
| Stabilization (1) | 30 to 37 | 20 sec. |
| Stabilization (2) | 30 to 37 | 20 sec. |
| Stabilization (3) | 30 to 37 | 20 sec. |
| Stabilization (4) | 30 to 37 | 30 sec. |
| Drying | 70 to 85 | 60 sec. |

The stabilization steps were performed in accordance with a so-called countercurrent replenishing process, in which the replenisher current flew in the direction from the stabilization tank (4) to the stabilization tank (1).

The compositions of the processing solutions were as follows:

| Color Developer: | |
|---|---|
| Water | 800 ml |
| Ethylenediaminetetraacetic acid | 2.0 g |
| Triethanolamine | 8.0 g |
| Sodium chloride | 1.4 g |
| Potassium carbonate | 25 g |
| N-Ethyl-N-(β-methanesulfonamidoethyl)-3-methyl-4-aminoaniline sulfate | 5.0 g |
| N,N-Diethylhydroxylamine | 4.2 g |
| 5,6-Dihydroxybenzene-1,2,4-trisulfonic acid | 3.3 g |
| Brightening agent (4,4'-diaminostilbene type) | 2.0 g |
| Water to make | 1,000 ml |
| pH (at 25° C.) | 10.10 |
| Bleach-Fix Bath: | |
| Water | 400 ml |
| Ammonium thiosulfate (70% aqueous solution) | 100 ml |
| Sodium sulfite | 18 g |
| Ethylenediaminetetraacetic acid iron(III) ammonium | 55 g |
| Disodium ethylenediamine-tetraacetate | 3 g |
| Glacial acetic acid | 8 g |
| Water to make | 1,000 ml |
| pH (at 25° C.) | 5.5 |
| Stabilizing Bath | |
| Formaldehyde (37% aqueous solution) | 0.1 g |
| Formaldehyde-sulfite adduct | 0.7 g |
| 5-Chloro-2-methyl-4-isothiazolin-3-one | 0.02 g |
| 2-Methyl-4-isothiazoline-3-one | 0.01 g |
| Copper sulfate | 0.005 g |
| Water to make | 1,000 ml |
| pH (at 25° C.) | 4.0 |

Green light reflection densities of the processed samples were measured, and the relative sensitivities and maximum densities were determined therefrom. The results obtained are shown in Table 1. As can be seen from Table 1, all the samples containing the magenta couplers of the present invention, from 104 to 113, showed high relative sensitivity and high maximum density, that is, excellent color developability.

TABLE 1

| Sample | Coupler | Relative Sensitivity | Maximum Density |
|---|---|---|---|
| 101 | A | 71 | 1.63 |
| 102 | B | 54 | 1.12 |
| 103 | C | 87 | 1.93 |
| 104 | M-1 | 103 | 2.43 |
| 105 | M-3 | 99 | 2.39 |
| 106 | M-4 | 101 | 2.41 |
| 107 | M-5 | 102 | 2.42 |
| 108 | M-6 | 98 | 2.40 |
| 109 | M-8 | 100 | 2.38 |
| 110 | M-14 | 102 | 2.39 |
| 111 | M-11 | 97 | 2.41 |
| 112 | M-17 | 98 | 2.38 |
| 113 | M-19 | 101 | 2.42 |

Coupler A

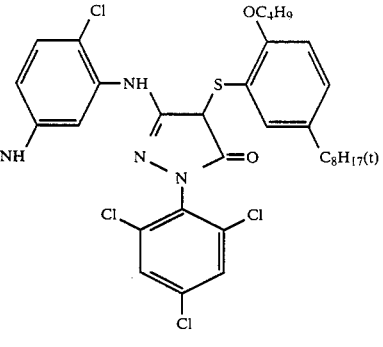

Coupler B

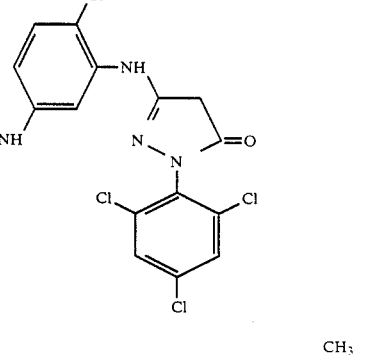

Coupler C

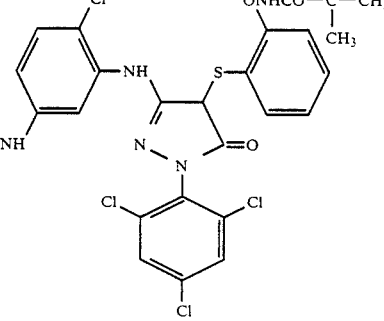

EXAMPLE 2

A paper support laminated with a polyethylene film on both sides thereof, were coated with the layers described below in this order to prepare a multilayer color photographic paper (Sample 201). The coating compositions were prepared in the manners described hereinbelow.

PREPARATION OF COATING COMPOSITION OF FIRST LAYER

To 19.1 g of a yellow coupler (ExY), 4.4 of a color image stabilizer (Cpd-1) and 0.7 g of a color image stabilizer (Cpd-7), were added 27.2 ml of ethyl acetate and 8.2 g of a solvent (Solv-3) to make a solution. The solution was emulsified and dispersed in 185 ml of a 10% aqueous gelatin solution containing 8 ml of a 10% sodium dodecylbenzenesulfonate solution. Separately, two kinds of blue-sensitive sensitizing dyes illustrated below were added to a silver chlorobromide emulsion (having a grain size of 0.85 micron and a cubic grain form with a variation coefficient of 0.07, and containing 1 mol% of silver bromide in such a condition as to be locally present at a part of the grain surface) each in an amount of $2.0 \times 10^{-4}$ mole per mole of silver, and then subjected to sulfur sensitization. The resulting silver chlorobromide emulsion was mixed homogeneously with the above-described emulsified dispersion, and further adjusted so that the resulting emulsion might have the composition described below. Thus, the coating composition for the first layer was prepared.

Coating compositions for the second to the seventh layers were prepared in the same manner as that for the first layer. In each layer, the sodium salt of 1-oxy-3,5-dichloro-s-triazine was contained therein as a gelatin hardener.

A sensitizing dye used in each emulsion layer is illustrated below.

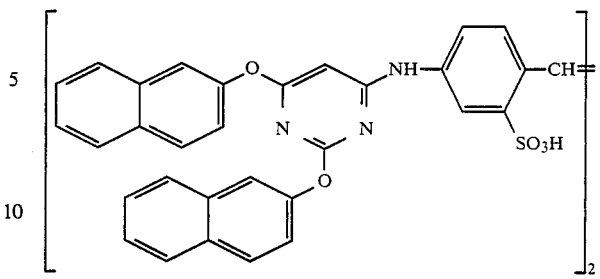

In addition, 1-(5-methylureidophenyl)-5-mercaptotetrazole was added to the blue-sensitive, the green-sensitive and the red-sensitive emulsion layers in amounts of $8.5 \times 10^{-5}$ mole, $7.7 \times 10^{-4}$ mole and $2.5 \times 10^{-4}$ mole, respectively, per mole silver halide.

Blue-Sensitive Emulsion Layer

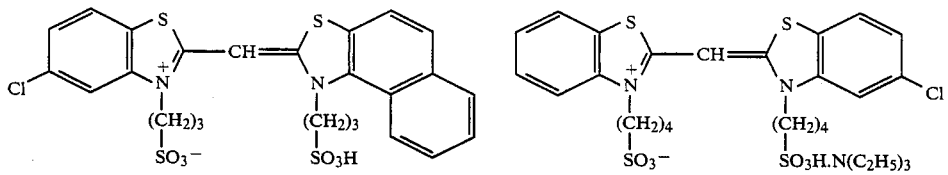

(The above-illustrated two kinds of dyes were each added in an amount of $2.0 \times 10^{-4}$ mole per mole of silver halide.)

Green-Sensitive Emulsion Layer

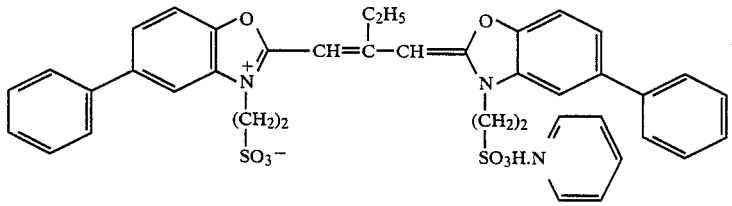

(added in an amount of $4.0 \times 10^{-4}$ mole per mole of silver halide) and

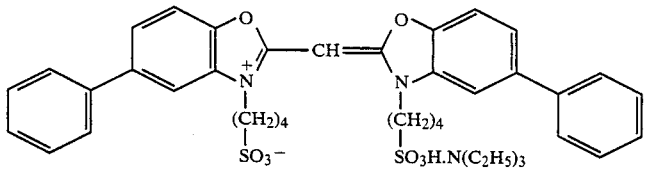

(added in an amount of $7.0 \times 10^{-5}$ mole per mole of silver halide).

Red-Sensitive Emulsion Layer

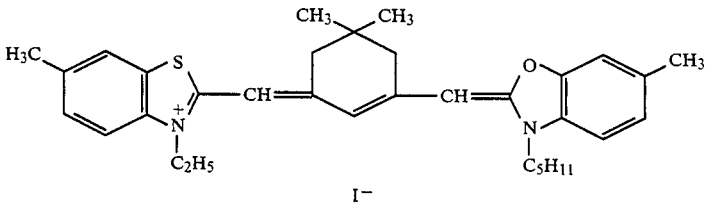

(added in an amount of $0.9 \times 10^{-4}$ mole per mole of silver halide)

To the red-sensitive emulsion layer was further added the following compound in an amount of $2.6 \times 10^{-3}$ mole per mole of silver halide:

Further, the following dyes were added to each emulsion layer for the purpose of preventing of irradiation:

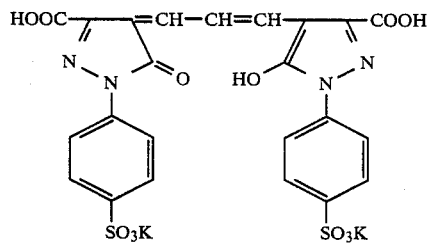

and

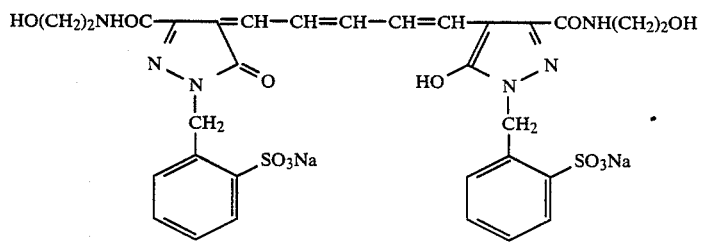

Constituent Layers:

The ingredients used in each layer and their coverages expressed in terms of g/m² are described below. In addition, only the coverage of the silver halide is expressed on a silver basis.

| Support | |
|---|---|
| Polyethylene-laminated paper (containing a white pigment (TiO₂) and a bluish dye (ultramarine) on the first layer side). | |
| First Layer (Blue-sensitive layer): | |
| Silver chlorobromide emulsion described above | 0.30 |
| Gelatin | 1.86 |
| Yellow coupler (ExY) | 0.82 |
| Color image stabilizer (Cpd-1) | 0.19 |
| Color image stabilizer (Cpd-7) | 0.03 |
| Solvent (Solv-3) | 0.35 |
| Second Layer (Color mixing inhibiting layer): | |
| Gelatin | 0.99 |
| Color mixing inhibitor (Cpd-5) | 0.08 |
| Solvent (Solv-1) | 0.16 |
| Solvent (Solv-4) | 0.08 |
| Third Layer (Green-sensitive layer): | |
| Silver chlorobromide emulsion (having a grain size of 0.4 micron and a cubic grain form with a variation coefficient of 0.09, and containing 1 mol % of bromide in such a condition as to be present locally at a part of grain surface) | 0.20 |
| Gelatin | 1.24 |
| Magenta coupler (as A in Example 1) | 0.29 |
| Color image stabilizer (Cpd-3) | 0.09 |
| Color image stabilizer (Cpd-4) | 0.06 |
| Solvent (Solv-2) | 0.32 |
| Solvent (Solv-7) | 0.16 |
| Fourth Layer (Ultraviolet absorbing layer): | |
| Gelatin | 1.58 |
| Ultraviolet absorbent (UV-1) | 0.47 |
| Color mixing inhibitor (Cpd-5) | 0.05 |
| Solvent (Solv-5) | 0.24 |
| Fifth Layer (Red-sensitive layer): | |
| Silver chlorobromide emulsion (having a grain size of 0.3 micron and a cubic grain form with a variation coefficient of 0.11, and containing 1.6 mol % of silver bromide in such a condition as to be present locally at a part of grain surface) | 0.21 |
| Gelatin | 1.34 |
| Cyan coupler (ExC) | 0.34 |
| Color image stabilizer (Cpd-6) | 0.17 |
| Color image stabilizer (Cpd-7) | 0.34 |
| Color image stabilizer (Cpd-9) | 0.04 |
| Solvent (Solv-4) | 0.37 |
| Sixth Layer (Ultraviolet absorbing layer): | |
| Gelatin | 0.53 |
| Ultraviolet absorbent (UV-1) | 0.16 |
| Color mixing inhibitor (Cpd-5) | 0.02 |
| Solvent (Solv-5) | 0.08 |
| Seventh Layer (Protective layer): | |
| Gelatin | 1.33 |
| Acryl modified copolymer of polyvinyl alcohol (modification degree: 17%) | 0.17 |
| Liquid paraffin | 0.03 |

The structural formulae of the compounds employed are illustrated below:

(ExY) Yellow Coupler
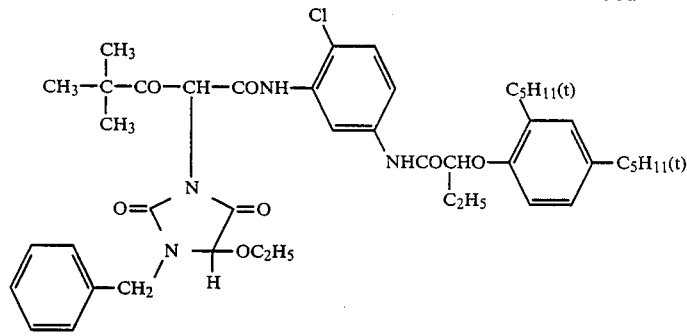
(ExC) Cyan Coupler
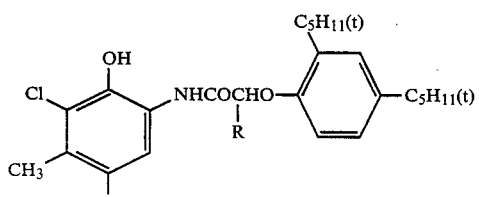
1:3:6 (by weight) mixture of the cyan couplers containing H, $C_2H_5$ and $C_4H_9$, respectively, as R.
(Cpd-1) Color Image Stabilizer
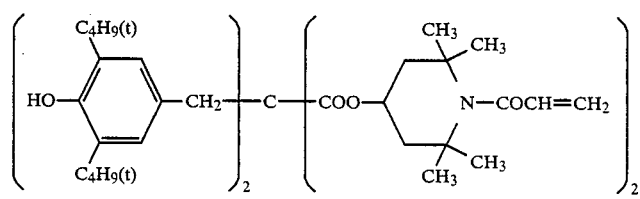
(Cpd-3) Color Image Stabilizer
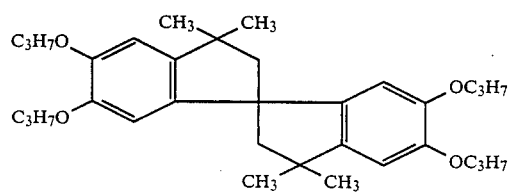
(Cpd-4) Color Image Stabilizer
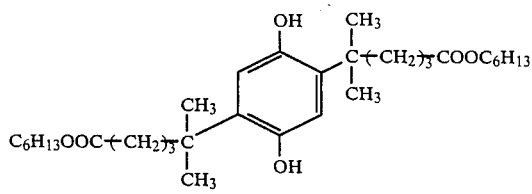
(Cpd-5) Color Mixing Inhibitor
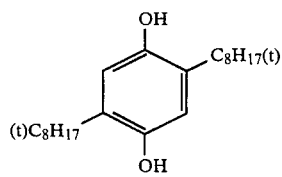
(Cpd-6) Color Image Stabilizer
2:4:4 (by weight) mixture of

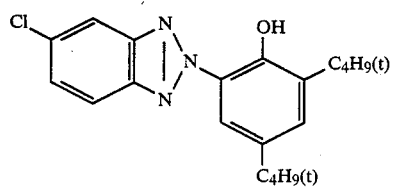
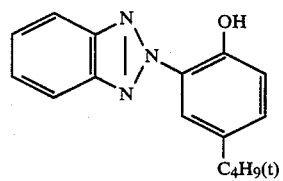
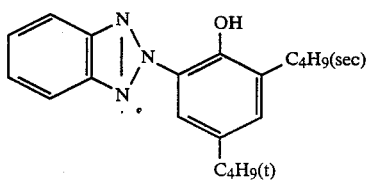
(Cpd-7) Color Image Stabilizer
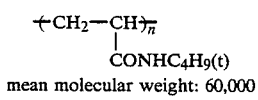
mean molecular weight: 60,000
(Cpd-9) Color Image Stabilizer
1:1:1 (by weight) mixture of
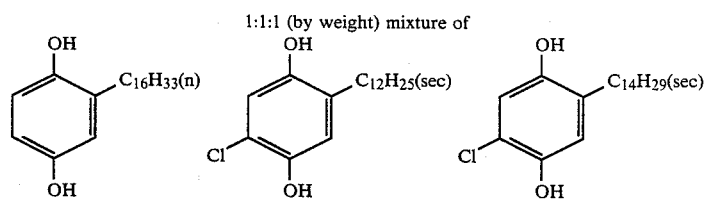
(UV-1) Ultraviolet Absorbent
4:2:4 (by weight) mixture of
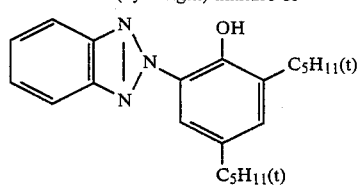
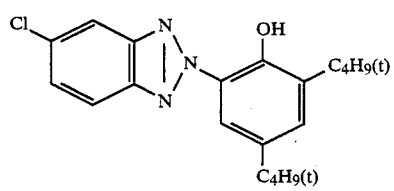
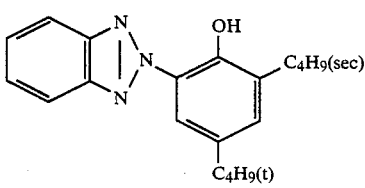
(Solv-1) Solvent (Solv-4)

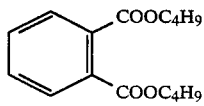

(Solv-2) Solvent

3:7 (by volume) mixture of

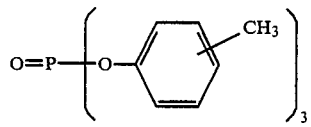

(Solv-3) Solvent $O=P(-O-C_9H_{19}(iso))_3$ (Solv-4) Solvent

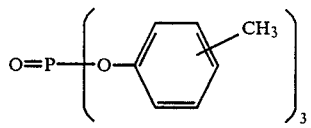

(Solv-5) Solvent

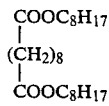

(Solv-6) Solvent

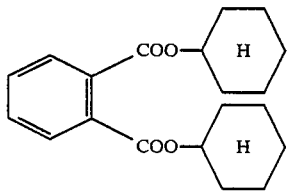

(Solv-7) Solvent

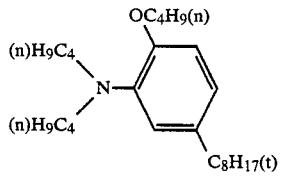

Sample 202 was prepared in the same manner as Sample 201, except the magenta coupler used in the third layer was changed to the M-8 coupler of the present invention.

These light-sensitive materials were each exposed through an optical wedge, and then subjected to a photographic process comprising the following steps:

| Processing Step | Temperature (°C.) | Time |
|---|---|---|
| Color Development | 35 | 45 sec. |

| Processing Step | Temperature (°C.) | Time |
|---|---|---|
| Bleach-Fix | 35 | 45 sec. |
| Washing (1) | 35 | 30 sec. |
| Washing (2) | 35 | 30 sec. |
| Washing (3) | 35 | 30 sec. |
| Drying | 75 | 60 sec. |

The compositions of the processing solutions used were as follows:

| Color Developer: | |
| --- | --- |
| Water | 800 ml |
| Ethylenediamine-N,N,N',N'-tetra-methylenephosphonic acid | 3.0 g |
| Triethanolamine | 8.0 g |
| Sodium chloride | 1.4 g |
| Potassium carbonate | 25 g |
| N-Ethyl-N-(β-methanesulfonamidoethyl)-3-methyl-4-aminoaniline sulfate | 5.0 g |
| N,N-bis(carboxymethyl)hydrazine | 5.0 g |
| Brightening agent (WHITEX 4B, produced by Sumitomo Chemical Co., Ltd.) | 1.0 g |
| Water to make | 1,000 ml |
| pH (at 25° C.) | 10.05 |
| Bleach-Fix Bath: | |
| Water | 700 ml |
| Ammonium thiosulfate (700 g/l aqueous solution) | 100 ml |
| Ammonium sulfite | 18 g |
| Ammonium ethylenediaminetetra-acetatoferrate(III) dihydrate | 55 g |
| Disodium ethylenediaminetetraacetate | 3 g |
| Ammonium bromide | 40 g |
| Glacial acetic acid | 8 g |
| Water to make | 1,000 ml |
| pH (at 25° C.) | 5.5 |

Washing Bath:
City water processed with an ion exchange resin until the calcium ion and the magnesium ion concentrations were each reduced to below 3 ppm (conductivity at 25° C.: 5 μs/cm) was used.

While the green light maximum density of Sample 201 was 1.55, that of Sample 202 was 2.40. Accordingly, the coupler of this invention has proved to exhibit excellent color developability even in such a rapid processing system as described above.

The remaining samples are prepared in the same manner as sample 202, except other magenta couplers of the present invention were used such as M-1, M-2, M-4, M-11 and M-14, respectively in the place of M-8, brought about similar results as that of sample 202.

EXAMPLE 3

A paper support laminated with a polyethylene film on both sides thereof were coated with the layers described below to prepare a multilayer color photographic paper (Sample 301). Coating compositions were prepared in the manner described hereinbelow.

Preparation of Coating Composition for First layer:

To 60.0 g of a yellow coupler (ExY) and 28.0 g of a discoloration inhibitor (Cpd-1) were added 150 ml of ethyl acetate, 1.0 ml of a solvent (Solv-3) and 3.0 ml of a solvent (Solv-4) to make a solution. The solution was added to 450 ml of a 10% aqueous gelatin solution containing sodium dodecylbenzenesulfonate and is dispersed thereinto with an ultrasonic homogenizer. The thus obtained dispersion was homogeneously mixed with 420 g of a silver chlorobromide emulsion containing the following blue-sensitive sensitizing dye (bromide content: 0.7 mol%) to prepare a coating composition for the first layer.

Coating compositions for the second to the seventh layers were prepared in the same manner as that for the first layer. In each layer, 1,2-bis(vinylsulfonyl)ethane was used as a gelatin hardener.

The following compounds were used as a sensitizing dye for each emulsion layer:

Blue-sensitive emulsion layer:
Anhydro-5,5'-dichloro-3,3'-disulfoethylthiacyanine hydroxide Green-sensitive emulsion layer:
Anhydro-9-ethyl-5,5'-di-phenyl-3,3'-disulfoethyl-oxacarbocyanine hydroxide Red-sensitive emulsion layer:
3,3'-Diethyl-5-methoxy-9,9'(2,2'-dimethyl-1,3-propano)thiacarbocyanine iodide In addition, a 7:2:1 (by mole) mixture of 1-(2-acetaminophenyl)-5-mercaptotetrazole, 1-phenyl-5-mercaptotetrazole and 1-(p-methoxyphenyl)-5-mercaptotetrazole was used as a stabilizer for each layer. Further, disodium [3-carboxy-5-hydroxy-4-(3-(3-carboxy-5-oxo-1-(2,5-disulfonatophenyl)-2-pyrazoline-4-ylidene)-1-propenyl)-1-pyrazolyl]benzene-2,5-disulfonate, tetrasodium N,N'-(4,8-dihydroxy-9,10-dioxo-3,7-disulfonatoanthracene-1,5-diyl)bis(aminomethanesulfonate), and sodium [3-cyano-5-hydroxy-4-(3-(3-cyano-5-oxo-1-(4-sulfonatophenyl)-2-pyrazoline-4-ylidene)-1-pentanyl)-1-pyrazolyl]benzene-4-sulfonate were used as irradiation preventing dyes.

Constituent Layers:
The ingredients used in each layer and their coverages expressed in terms of $g/m^2$ are described below. In addition, only the coverage of the silver halide is expressed on a silver basis.

| Support: | |
| --- | --- |
| Paper support laminated with polyethylene on both sides | |
| First Layer (Blue-sensitive layer): | |
| Silver chlorobromide emulsion described above (AgBr: 0.7 mol %, crystal form: cube, grain size: 0.9 micron) | 0.29 |
| Gelatin | 1.80 |
| Yellow coupler (ExY) | 0.60 |
| Discoloration inhibitor (Cpd-1) | 0.28 |
| Solvent (Solv-3) | 0.01 |
| Solvent (Solv-4) | 0.03 |
| Second Layer (Color mixing inhibiting layer): | |
| Gelatin | 0.80 |
| Color mixing inhibitor (Cpd-2) | 0.055 |
| Solvent (Solv-1) | 0.03 |
| Solvent (Solv-2) | 0.015 |
| Third Layer (Green-sensitive layer): | |
| Silver chlorobromide emulsion (AgBr: 0.7 mol %, crystal form: cube, grain size: 0.45 micron) | 0.21 |
| Gelatin | 1.40 |
| Magenta coupler (ExM) | 0.67 |
| Discoloration inhibitor (Cpd-3) | 0.23 |
| Discoloration inhibitor (Cpd-4) | 0.11 |
| Solvent (Solv-1) | 0.20 |
| Solvent (Solv-2) | 0.02 |
| Fourth Layer (Color mixing inhibiting layer): | |
| Gelatin | 1.70 |
| Color mixing inhibitor (Cpd-2) | 0.065 |
| Ultraviolet absorbent (UV-1) | 0.45 |
| Ultraviolet absorbent (UV-2) | 0.23 |
| Solvent (Solv-1) | 0.05 |
| Solvent (Solv-2) | 0.05 |
| Fifth Layer (Red-sensitive layer): | |
| Silver chlorobromide emulsion (AgBr: 4 mol %, crystal form: cube, grain size: 0.5 micron) | 0.21 |
| Gelatin | 1.80 |
| Cyan coupler (ExC-1) | 0.26 |
| Cyan coupler (ExC-2) | 0.12 |
| Discoloration inhibitor (Cpd-1) | 0.20 |
| Solvent (Solv-1) | 0.16 |
| Solvent (Solv-2) | 0.09 |
| Sixth Layer (Ultraviolet absorbing layer): | |
| Gelatin | 0.70 |
| Ultraviolet absorbent (UV-1) | 0.26 |
| Ultraviolet absorbent (UV-2) | 0.07 |

| | |
|---|---|
| -continued | |
| Solvent (Solv-1) | 0.30 |
| Solvent (Solv-2) | 0.09 |
| Seventh Layer (Protective layer): | |
| Gelatin | 1.07 |

(ExY) Yellow coupler: α-Pivaryl-α-(3-benzyl-1-hydantoinyl)-2-chloro-5-[(β-dodecylsulfonyl)butylamido]acetanilide
(ExM) Magenta coupler: 1-(2,4,6-Trichlorophenyl-3-[2-chloro-5-(3-octadecenylsuccinimido)anilino]-5-pyrazolone
(ExC-1) Cyan coupler: 2-Pentafluorobenzamido-4-chloro-5-[2-(2,4-di-tert-aminophenoxy)-3-methylbutylamido]phenol
(ExC-2) Cyan coupler: 2,4-Dichloro-3-methyl-6-[α-(2,4-di-tert-amylphenoxy)-butylamido]phenol
(Cpd-1) Discoloration inhibitor: 2-(2-hydroxy-3,5-di-tert-amylphenyl)benztriazole
(Cpd-2) Color mixing inhibitor: 2,5-Di-tert-octylhydroquinone
(Cpd-3) Discoloration inhibitor: 1,4-Di-tert-amyl-2,5-dioctyloxybenzene
(Cpd-4) Discoloration inhibitor: 2,2'-Methylenebis(4-methyl-6-tert-butylphenol)
(Cpd-5) p-(p-Toluenesulfonamido)phenyl-dodecane:
(Solv-3) Solvent: Dinonyl phthalate
(Solv-4) Solvent: N,N-Diethylcarbonamido-methoxy-2,4-di-tert-amylbenzene
(UV-1) Ultraviolet absorbent: 2-(2-Hydroxy-3,5-di-tert-amylphenyl)benzotriazole
(UV-2) Ultraviolet absorbent: 2-(2-Hydroxy-3,5-di-tert-butylphenyl)benzotriazole
(Solv-1) Solvent: Di-(2-ethylhexyl)phthalate
(Solv-2) Solvent: Dibutyl phthalate Sample 302 was prepared in the same manner as sample 301, except the magenta coupler used in the third layer was changed to M-1 coupler of the present invention. These samples were processed in the same manner as in Example 1.

While the green light maximum density of Sample 301 was 1.26, that of Sample 302 was 2.42. Accordingly, the coupler of the present invention has proved to exhibit excellent color developability even in a rapid processing system as described above.

The samples prepared in the same manner as sample 302, except using other magenta couplers of the present invention, such as M-2, M-5, M-6, M-7, M-9 and M-17, respectively in the place of M-1, brought about similar results as that of sample 302.

EXAMPLE 4

A paper support laminated with a polyethylene film on both sides thereof coated with the layers described below in the order given to prepare a multilayer color photographic paper (Sample 401). Coating compositions were prepared in the manner described hereinbelow.

Preparation of Coating Composition for First Layer:

To 19.1 g of a yellow coupler (ExY), 4.4 g of a color image stabilizer (Cpd-1) and 1.8 g of a color image stabilizer (Cpd-7), were added 27.2 ml of ethyl acetate, 4.1 g of a solvent (Solv-3) and 4.1 g of the other solvent (Solv-6) to make a solution. The solution was emulsified and dispersed in 185 ml of a 10% aqueous gelatin solution containing 8 ml of a 10% sodium dodecylbenzenesulfonate solution. Separately, a silver chlorobromide emulsion (a 1:3 (by Ag mole) mixture of a silver chlorobromide emulsion having a bromide content of 80.0 mol%, a crystal form of a cube, an average grain size of 0.85 micron and a variation coefficient of 0.08, and a silver chlorobromide emulsion having a bromide content of 80.0 m mol%, a crystal form of a cube, an average grain size of 0.62 micron and a variation coefficient of 0.07) was subjected to sulfur sensitization, and the following blue-sensitive sensitizing dye is added thereto in an amount of $5.0 \times 10^{-4}$ mole per mole of silver. The resulting silver chlorobromide emulsion was mixed homogeneously with the above-described emulsified dispersion, and then further adjusted so that the resulting emulsion has the composition described below. Thus, the coating composition for the first layer was prepared.

The coating compositions for the second to the seventh layers were prepared in the same manner as that for the first layer. In each layer, the sodium salt of 1-oxy-3,5-dichloro-s-triazine was included therein as the gelatin hardener.

The sensitizing dye used in each emulsion layer is illustrated below:

Blue-Sensitive Emulsion Layer

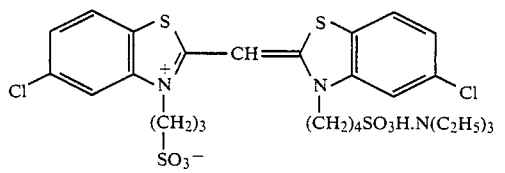

(added in an amount of $5.0 \times 10^{-4}$ mole per mole of silver halide.)

Green-Sensitive Emulsion Layer

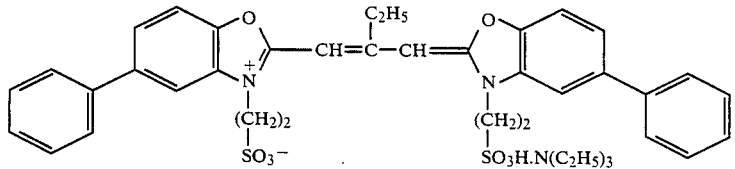

(added in an amount of $4.0 \times 10^{-4}$ mole per mole of silver halide.)
and

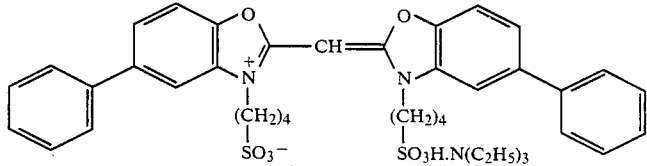

(added in an amount of $7.0 \times 10^{-5}$ mole per mole of silver halide.)

Red-Sensitive Emulsion Layer

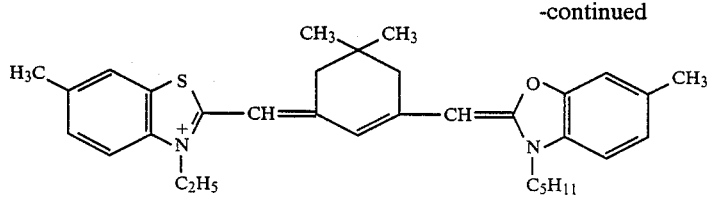

(added in an amount of 0.9 × 10$^{-4}$ mole per mole of silver halide.)

To the red-sensitive emulsion layer was further added the following compound in an amount of 2.6×10$^{-3}$ mole per mole of silver halide:

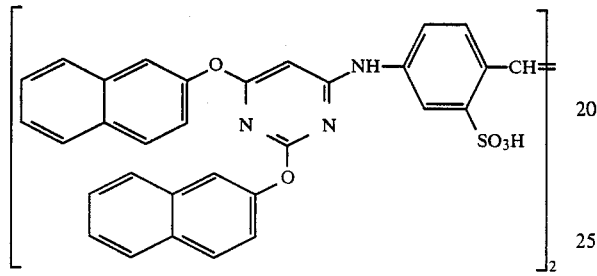

In addition, 1-(5-methylureidophenyl)-5-mercaptotetrazole was added to the blue-sensitive, the green-sensitive and the red-sensitive emulsion layers in amounts of 4.0×10$^{-6}$ mole, 3.0×10$^{-5}$ mole and 1.0×10$^{-5}$ mole, respectively, per mole of silver halide. Further, 2-methyl-5-t-octylhydroquinone was added to those emulsion layers in amounts of 8×10$^{-3}$ mole, 2×10$^{-2}$ mole and 2×10$^{-2}$ mole, respectively, per mole of silver halide.

Furthermore, the following dyes were added to each emulsion layer for the purpose of preventing irradiation:

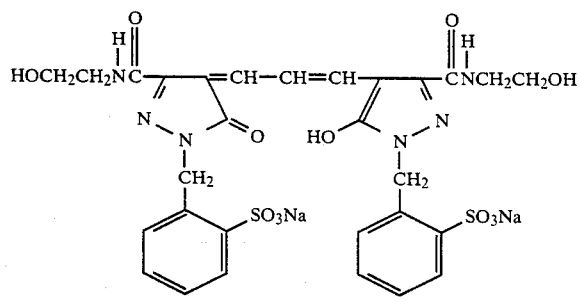

and

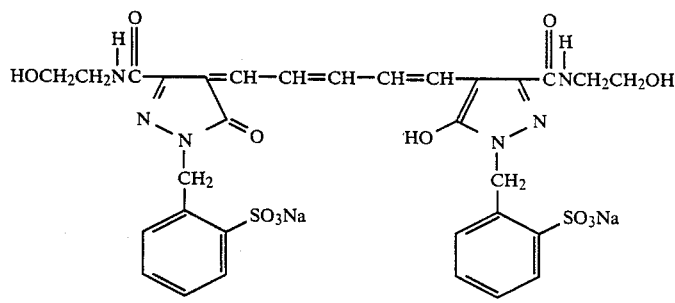

Constituent Layers:

The ingredients used in each layer and their coverages expressed in terms of g/m$^2$ are described below. In addition, only the coverage of the silver halide is expressed on a silver basis.

| Support | |
|---|---|
| Polyethylene-laminated paper (containing a white pigment (TiO$_2$) and a bluish dye (ultramarine) on the first layer side). | |
| First Layer (Blue-sensitive layer) | |
| Silver chlorobromide emulsion described above (AgBr: 80 mol %) | 0.26 |
| Gelatin | 1.83 |
| Yellow coupler (ExY) | 0.83 |
| Color image stabilizer (Cpd-1) | 0.19 |
| Color image stabilizer (Cpd-7) | 0.08 |
| Solvent (Solv-3) | 0.18 |
| Solvent (Solv-6) | 0.18 |
| Second Layer (Color mixing inhibiting layer) | |
| gelatin | 0.99 |
| Color stain inhibitor (Cpd-6) | 0.08 |
| Solvent (Solv-1) | 0.16 |
| Solvent (Solv-4) | 0.08 |
| Third Layer (Green-sensitive layer) | |
| Silver chlorobromide emulsion (1:1 (by Ag mole) mixture of a silver chlorobromide emulsion having a silver bromide content of 90 mol %, a crystal form of a cube, an average grain size of 0.47 micron and a variation coefficient of 0.12, and a silver chlorobromide emulsion having a silver bromide content of 90 mol %, a crystal form of a cube, an average grain size of 0.36 micron and a variation coefficient of 0.09) | 0.16 |
| Gelatin | 1.79 |
| Magenta coupler (A in Example 1) | 0.32 |

| | |
|---|---|
| Color image stabilizer (Cpd-3) | 0.20 |
| Color image stabilizer (Cpd-8) | 0.03 |
| Color image stabilizer (Cpd-4) | 0.01 |
| Color image stabilizer (Cpd-9) | 0.04 |
| Solvent (Solv-2) | 0.65 |
| Fourth Layer (Ultraviolet absorbing layer) | |
| gelatin | 1.58 |
| Ultraviolet absorbent (UV-1) | 0.47 |
| Color mixing inhibitor (Cpd-5) | 0.05 |
| Solvent (Solv-5) | 0.24 |
| Fifth Layer (Red-sensitive layer) | |
| Silver chlorobromide emulsion (1:2 (by Ag mole) mixture of a silver chlorobromide emulsion having a silver bromide content of 70 mol %, a crystal form of a cube, an average grain size of 0.49 micron and a variation coefficient of 0.08, and a silver chlorobromide emulsion having a silver bromide content of 70 mol %, a crystal form of a cube, an average grain size of 0.34 micron and a variation coefficient of 0.10) | 0.23 |
| Gelatin | 1.34 |
| Cyan coupler (ExC) | 0.30 |
| Color image stabilizer (Cpd-6) | 0.17 |
| Color image stabilizer (Cpd-7) | 0.40 |
| Solvent (Solv-6) | 0.20 |
| Sixth Layer (Ultraviolet absorbing layer) | |
| Gelatin | 0.53 |
| Ultraviolet absorbent (UV-1) | 0.16 |
| Color mixing inhibitor (Cpd-5) | 0.02 |
| Solvent (Solv-5) | 0.08 |
| Seventh Layer (Protective layer) | |
| Gelatin | 1.33 |
| Acryl modified copolymer of polyvinyl alcohol (modification degree: 17%) | 0.17 |
| Liquid paraffin | 0.03 |

The structural formulae of the compounds employed are illustrated below:

(Cpd-1) Color Image Stabilizer

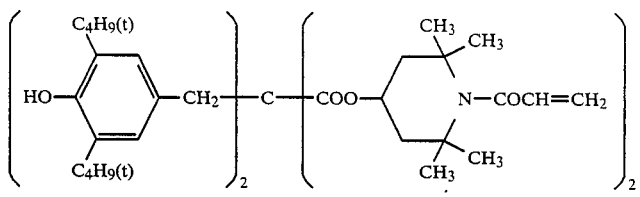

(Cpd-3) Color Image Stabilizer

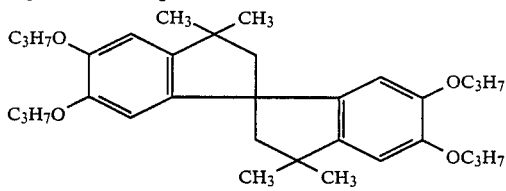

(Cpd-4) Color Image Stabilizer

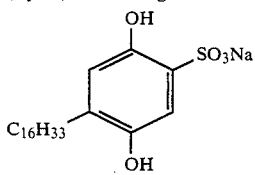

(Cpd-5) Color Mixing Stabilizer

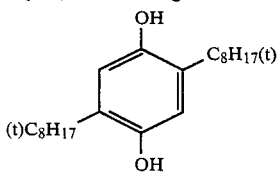

(Cpd-6) Color Image Stabilizer
2:4:4 (by weight) mixture of

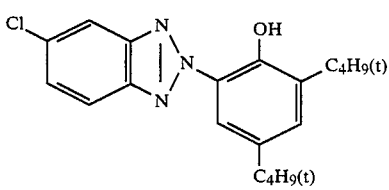

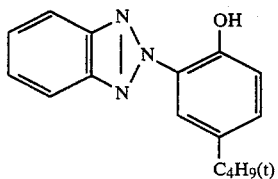
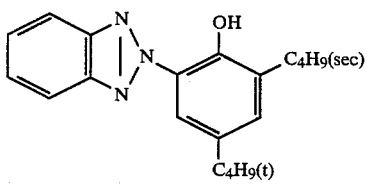
(Cpd-7) Color Image Stabilizer
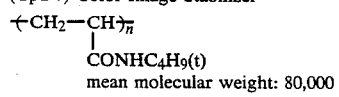
mean molecular weight: 80,000
(Cpd-8) Color Image Stabilizer
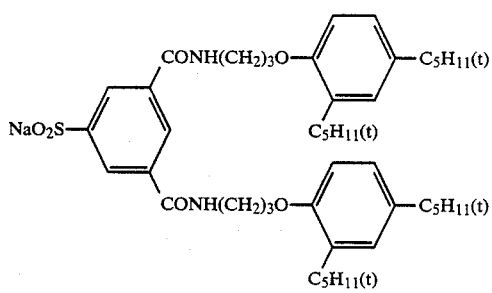
(Cpd-9) Color Image Stabilizer
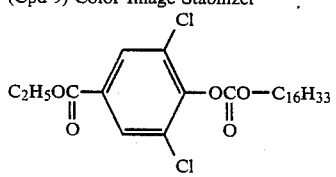
(UV-1) Ultraviolet absorbent
4:2:4 (by weight) mixture of
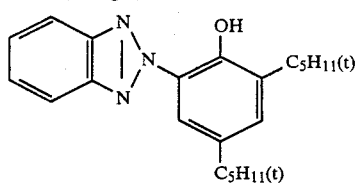
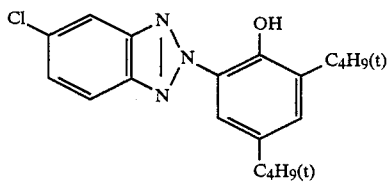
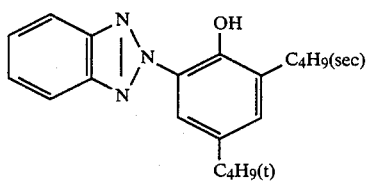

(Solv-1) Solvent
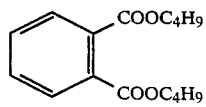
(Solv-2) Solvent
2:1 (by volume) mixture of
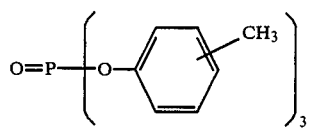
(Solv-3) Solvent
$O=P(\!-\!O\!-\!C_9H_{19}(iso))_3$
(Solv-4) Solvent
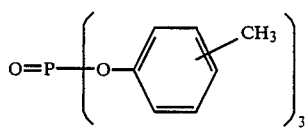
(Solv-5) Solvent
$\underset{\underset{\underset{COOC_8H_{17}}{|}}{\overset{\overset{COOC_8H_{17}}{|}}{(CH_2)_8}}}{}$
(Solv-6) Solvent
$C_8H_{17}\overset{\overset{O}{\diagup\!\diagdown}}{CHCH}(CH_2)_7COOC_8H_{17}$
(ExY) Yellow Coupler
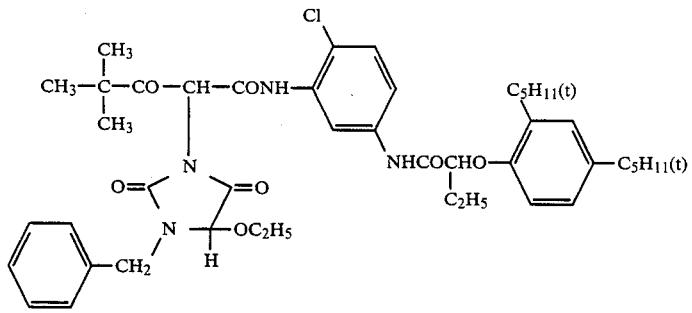
(ExC) Cyan Coupler
1:1 (by mole) mixture of
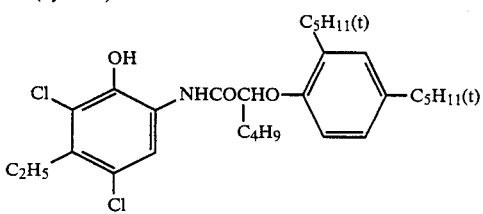

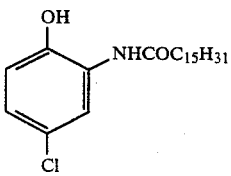

Samples 402 to 410 were prepared in the same manner as in Sample 401, except the magenta coupler used in the third layer was changed to the couplers set forth in Table 2.

These light-sensitive materials were each exposed through an optical wedge, and then subjected to the following photographic processing steps.

| Processing Step | Temperature (°C.) | Time |
|---|---|---|
| Color Development | 37 | 3 min. 30 sec. |
| Bleach-Fix | 33 | 1 min. 30 sec. |
| Washing | 24 to 34 | 3 min. |
| Drying | 70 to 80 | 1 min. |

The compositions of the processing solutions used were as follows:

| Color Developer | | |
|---|---|---|
| Water | 800 | ml |
| Diethylenetriaminepentaacetic acid | 1.0 | g |
| Nitrilotriacetic acid | 2.0 | g |
| 1-Hydroxyethylidene-1,1-diphosphonic acid (60% aqueous solution) | 1.0 | ml |
| Benzyl alcohol | 15 | ml |
| Diethylene glycol | 10 | ml |
| Sodium sulfite | 2.0 | g |
| Potassium bromide | 1.0 | g |
| Potassium carbonate | 30 | g |
| N Ethyl-N-(β-methanesulfonamidoethyl)-3-methyl-4-aminoaniline sulfate | 4.5 | g |
| Hydroxylamine sulfate | 3.0 | g |
| Brightening agent (WHITEX 4, produced by Sumitomo Chemical Co., Ltd.) | 1.0 | g |
| Water to make | 1,000 | ml |
| pH (at 25° C.) | 10.25 | |
| Bleach-Fix Bath | | |
| Water | 400 | ml |
| Ammonium thiosulfate (70% aqueous solution) | 150 | ml |
| Sodium sulfite | 18 | g |
| Ammonium ethylenediaminetetra-acetatoferrate(III) dihydrate | 55 | g |
| Disodium ethylenediaminetetraacetate | 5 | g |
| Water to make | 1,000 | ml |
| pH (at 25° C.) | 6.70 | |

Each of the samples in which the color images were formed in the above-described manner was subjected to a discoloration test by a 7 days exposure to a xenon tester (illuminance: 200,000 lux). The density measurement was carried out with a Fuji Auto-recording Densitometer, and each sample was examined for a density change in the area having an initial density of 1.0 prior to the test. The results obtained are shown in Table 2. As can be observed from the results in Table 2, the samples 402 to 410 containing the magenta couplers of the present invention, respectively, were superior in fastness to comparative sample 401.

TABLE 2

| Sample | Magenta Coupler | Light Fastness Test (xenon lamp, 7 days, $D_0 = 1.0$) (%)* |
|---|---|---|
| 401 | A (same as comparative coupler used in Example 1) | 74 |
| 402 | M-1 | 82 |
| 403 | M-2 | 80 |
| 404 | M-3 | 83 |
| 405 | M-4 | 82 |
| 406 | M-5 | 81 |
| 407 | M-6 | 83 |
| 408 | M-8 | 81 |
| 409 | M-13 | 81 |
| 410 | M-19 | 80 |

*: the rate of the density to $D_0$

EXAMPLE 5

A paper support laminated with a polyethylene film on both sides thereof, were coated with the layers described below in the order given to prepare a multilayer color photographic paper (Sample 501). The coating compositions were prepared in the manner described hereinbelow.

Preparation of Coating Composition for First Layer:

To 60.0 g of a yellow coupler (ExY) and 28.0 g of a discoloration inhibitor (Cpd-1) were added 150 ml of ethyl acetate, 3.0 ml of a solvent (Solv-3) and 1.5 ml of a solvent (Solv-2) to make a solution. The solution was added to 450 ml of a 10% aqueous gelatin solution containing sodium dodecylbenzenesulfonate, and dispersed thereinto with an ultrasonic homogenizer. The thus obtained dispersion was homogeneously mixed with 420 g of a silver chlorobromide emulsion (silver bromide content: 90.0 mol%) containing the following blue-sensitive sensitizing dye to prepare a coating composition for the first layer.

The coating compositions for the second to the seventh layers were prepared in the same manner as that for the first layer. In each layer, 1,2-bis(vinylsulfonyl)ethane was used as a gelatin hardener.

The following compounds were used as sensitizing dyes for their respectively emulsion layers:
Blue-sensitive emulsion layer:
Anhydro-5-methoxy-5'-methyl-3,3'-disulfopropyl-selenacyanine hydroxide
Green-sensitive emulsion layer:
Anhydro-9-ethyl-5,5'-di-phenyl-3,3'-disulfoethyloxacarbocyanine hydroxide
Red-sensitive emulsion layer:
3,3'-Diethyl-5-methoxy-9,9'-(2,2'-dimethyl-1,3-propano)thiacarbocyanine iodide In addition, 1-methyl-2-mercapto-5-acetylamino-1,3,4-triazole was used as a stabilizer for each layer.

Further, disodium [3-carboxy-5-hydroxy-4-(3-(3-carboxy-5-oxo-1-(2,5-disulfonatophenyl)-2-pyrazoline-4-ylidene)-1-propenyl)-1-pyrazolyl]benzene-2,5-disulfonate, and tetrasodium N,N'-(4,8-dihydroxy-9,10-dioxo- 3,7-disulfonatoanthracene-1,5-diyl)bis(aminomethanesulfonate) were used as irradiation preventing dyes.

Consituent Layers:

The ingredients used in each layer and their coverages expressed in terms of g/m$^2$ are described below. In addition, only the coverage of the silver halide is expressed on a silver basis.

| Support |  |
|---|---|
| Paper support laminated with polyethylene on both sides |  |
| First Layer (Blue-sensitive layer): |  |
| Silver halide emulsion (Br: 90%) | 0.29 |
| Gelatin | 1.80 |
| Yellow coupler (ExY) | 0.60 |
| Discoloration inhibitor (Cpd-1) | 0.28 |
| Solvent (Solv-1) | 0.03 |
| Solvent (Solv-2) | 0.015 |
| Second Layer (Color mixing inhibiting layer): |  |
| Gelatin | 0.80 |
| Color mixing inhibitor (Cpd-2) | 0.055 |
| Solvent (Solv-1) | 0.03 |
| Solvent (Solv-2) | 0.015 |
| Third Layer (Green-sensitive layer): |  |
| Silver halide emulsion (Br: 74%) | 0.305 |
| Gelatin | 1.40 |
| Magenta coupler (ExM) | 0.67 |
| Discoloration inhibitor (Cpd-3) | 0.23 |
| Discoloration inhibitor (Cpd-4) | 0.11 |
| Solvent (Solv-1) | 0.20 |
| Solvent (Solv-2) | 0.02 |
| Fourth Layer (Color mixing inhibiting layer): |  |
| Gelatin | 1.70 |
| Color mixing inhibitor (Cpd-2) | 0.065 |
| Ultraviolet absorbent (UV-1) | 0.45 |
| Ultraviolet absorbent (UV-2) | 0.23 |
| Solvent (Solv-1) | 0.05 |
| Solvent (Solv-2) | 0.05 |
| Fifth Layer (Red-sensitive layer): |  |
| Silver halide emulsion (Br: 74%) | 0.21 |
| Gelatin | 1.80 |
| Cyan coupler (ExC-1) | 0.26 |
| Cyan coupler (ExC-2) | 0.12 |
| Discoloration inhibitor (Cpd-1) | 0.20 |
| Solvent (Solv-1) | 0.16 |
| Solvent (Solv-2) | 0.09 |
| Sixth Layer (Ultraviolet absorbing layer): |  |
| Gelatin | 0.70 |
| Ultraviolet absorbent (UV-1) | 0.26 |
| Ultraviolet absorbent (UV-2) | 0.07 |
| Solvent (Solv-1) | 0.30 |
| Solvent (Solv-2) | 0.09 |
| Seventh Layer (Protective layer): |  |
| Gelatin | 1.07 |

(ExY) Yellow coupler: α-Pivaryl-α-(3-benzyl 1-hydantoinyl)-2-chloro-5-[γ-(2,4-di-tert-amylphenoxy)butylamido]-acetanilide
(ExM) Magenta coupler: 1-(2,4,6-Trichlorophenyl)-3-[2-chloro-5-(3-octadecenyl-succinimido)anilino]-5-pyrazolone
(ExC-1) Cyan coupler: 2-Pentafluorobenzamido-4-chloro-5-[2-(2,4-di-tert-aminophenoxy)-3-methylbutylamido]phenol
(ExC-2) Cyan coupler: 2,4-Dichloro-3-methyl-6-[α-(2,4-di-tert-amyl-phenoxy)-butylamido]phenol
(Cpd-1) Discoloration inhibitor: 2-(2-hydroxy-3,5-di-tert-butylphenyl)-benztriazole
(Cpd-2) Color mixing inhibitor: 2,5-Di-tert-octylhydroquinone
(Cpd-3) Discoloration inhibitor: 1,4-Di-tert-amyl-2,5-dioctyloxybenzene
(Cpd-4) Discoloration inhibitor: 2,2'-Methylenebis(4-methyl-6-tert-butylphenol)
(UV-1) Ultraviolet absorbent: 2-(2-Hydroxy-3,5-di-tert-amylphenyl(benzotriazole
(UV-2) Ultraviolet absorbent: 2-(2-Hydroxy-3,5-di-tert-butylphenyl)benzotriazole
(Solv-1) Solvent: Di(2-ethylhexyl) phthalate
(Solv-2) Solvent: Dibutyl phthalate Samples 502 to 510 were prepared in the same manner as the sample 501, except the magenta coupler used in the third layer was changed to the couplers of the present invention set forth in Table 3, respectively. These samples were processed in the same manner as in Example 4.

Each of the samples with the thus formed color images was subjected to a discoloration test by a 7 day exposure to a xenon tester (illuminance: 200,000 lux).

TABLE 3

| Sample | Magenta Coupler | Light Fastness Test (xenon lamp, 7 days, $D_0$ = 1.0) (%)* |
|---|---|---|
| 501 | ExM | 64 |
| 502 | A (same as comparative coupler used in Example 1) | 74 |
| 503 | M-1 | 81 |
| 504 | M-2 | 82 |
| 505 | M-3 | 82 |
| 506 | M-5 | 84 |
| 507 | M-6 | 81 |
| 508 | M-11 | 82 |
| 509 | M-14 | 83 |
| 510 | M-17 | 80 |

*: the rate of the density to $D_0$

The density measurement was carried out with a Fuji Auto-recording Densitometer, and each sample was examined for a density change in the area having an initial density of 1.0 prior to the test. The results obtained are shown in the above Table 3. As can be seen from Table 3, samples 503 to 510 containing the magenta couplers of the present invention, respectively, were superior in fastness to comparative samples 501 and 502.

Each of the couplers of the present invention has high sensitivity and provides high density of the developed color, and the magenta dye image derived therefrom is excellent in fastness to light.

In addition, each of the couplers provides high sensitivity and high density of the developed color even in a rapid processing system which utilizes silver halide emulsions having a high chloride content.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support and at least one silver halide photographic emulsion layer on the support, said emulsion layer containing a 5-pyrazolone coupler having a coupling eliminable group of the following general formula (I) at the coupling site thereof:

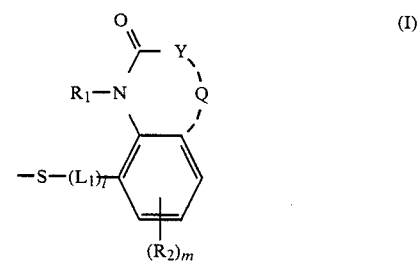

wherein $L_1$ represents a substituted or an unsubstituted methylene or ethylene group; l represents 0 or 1; m represents 0 or an integer from 1 to 3; $R_1$ represents a hydrogen atom, or a substituted or an unsubstituted alkyl, aryl or heterocyclic group; Y represents

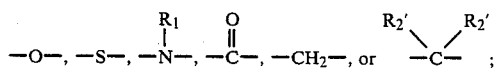

Q represents a single bond or nonmetal atoms necessary to complete a 5- to 8-membered ring together with

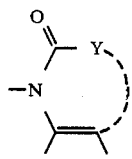

said 5- to 8-membered ring may further has a saturated or an unsaturated ring condensed thereto; $R_2$ represents a halogen atom, an alkyl group; an aryl group, an alkoxy group, an aryloxy group, an alkylthio group, an arylthio group, an alkylsulfonyl group, an arylsulfonyl group, an acylamino group, an alkoxycarbonylamino group, a sulfonamido group, a sulfamoyl group, an ureido group, an alkoxycarbonyl group, an aryloxycarbonyl group, an acyl group, a cyano group, a trifluoromethyl group, an amino group, an N-alkylamino group, an N-arylamino group, an N,N-dialkylamino group, a diacylamino group, an imido group or a carbamoyl group, and when m represents 2 or 3, $R_2$ groups may be the same or different; $R_2'$ represents a hydrogen atom, or has the same meaning as $R_2$ and two $R_2'$ groups may be linked to form a 5- to 7-membered saturated or unsaturated ring; and —Y—Z— may be a substituted or an unsubstituted carbon-carbon or carbon-nitrogen double bond.

2. The silver halide color photographic light-sensitive material of claim 1, wherein the substituted methylene, ethylene, alkyl, aryl and heterocyclic groups each has a substituent selected from the group consisting of a halogen atom, an alkyl group, an aryl group, an alkoxy group, an aryloxy group, an alkylthio group, an arylthio group, an alkylsulfonyl group, an arylsulfonyl group, an acylamino group, an alkoxycarbonylamino group, a sulfonamido group, a sulfamoyl group, an ureido group, an alkoxycarbonyl group, an aryloxycarbonyl group, an acyl group, a cyano group, a trifluoromethyl group, an amino group, an N-alkylamino group, an N-arylamino group, an N,N-dialkylamino group, a diacylamino group, an imido group or a carbamoyl group.

3. The silver halide color photographic light-sensitive material of claim 1, wherein the system in said coupling eliminable group represented by formula (I) is a group selected from the group consisting of the following formulas (1) to (26):

(1)

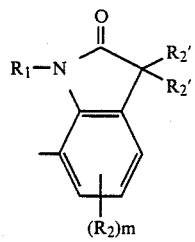

(2)

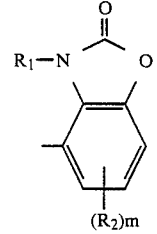

(3)

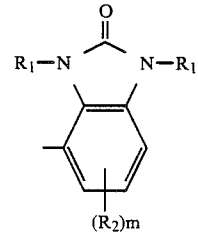

(4)

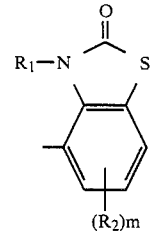

(5)

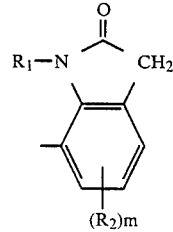

(6)

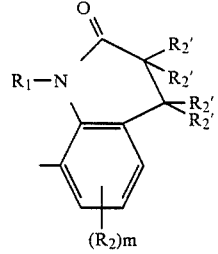

(7)

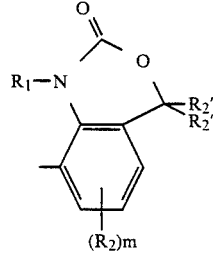

-continued
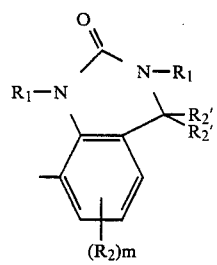 (8)
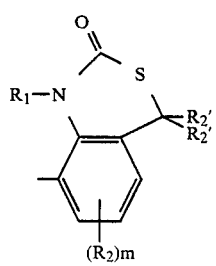 (9)
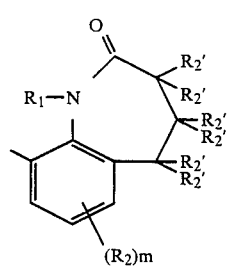 (10)
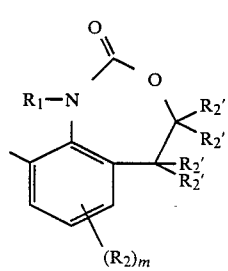 (11)
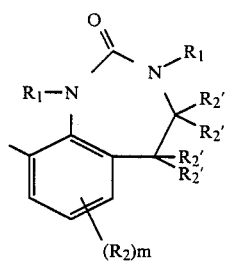 (12)
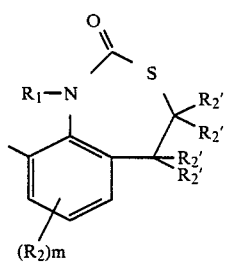 (13)
-continued
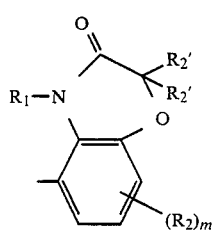 (14)
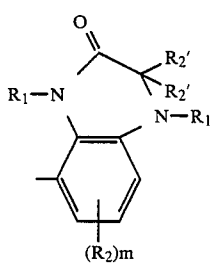 (15)
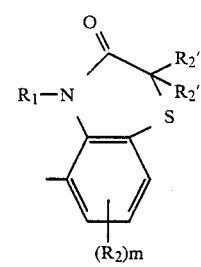 (16)
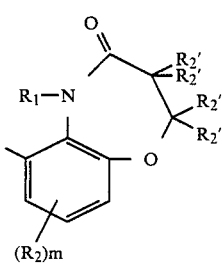 (17)
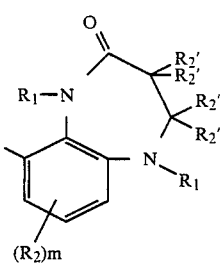 (18)
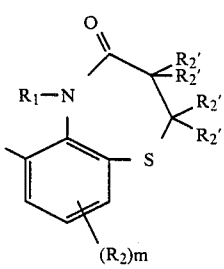 (19)

-continued

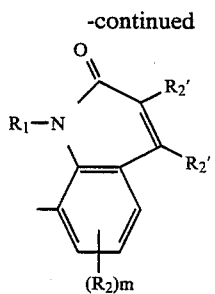 (20)

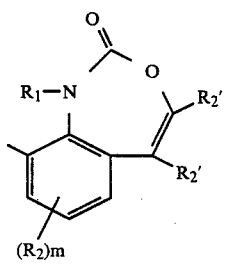 (21)

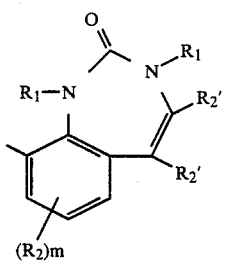 (22)

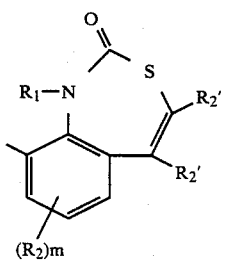 (23)

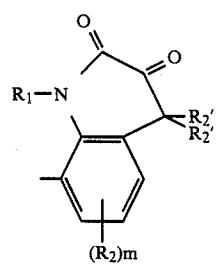 (24)

-continued

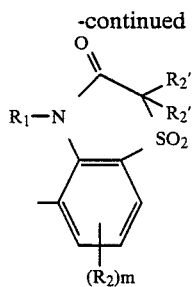 (25)

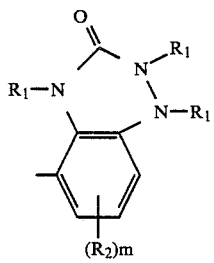 (26)

wherein each symbols mean the same as those in claim 1.

4. The silver halide color photographic light-sensitive material of claim 1, wherein l is 0 and $R_1$ is a hydrogen atom.

5. The silver halide color photographic light-sensitive material of claim 1, wherein 5-pyrazolone coupler is represented by general formula (II):

$$R^{21}-NH \quad Z_{21} \atop N-N \atop Ar \quad =O \qquad (II)$$

wherein $R^{21}$ represents a substituted or unsubstituted alkyl, aryl, acyl, or carbamoyl group; Ar represents a phenyl group, or a phenyl group substituted by at least one halogen atom, alkyl group, cyano group, alkoxy group, alkoxycarbonyl group or acylamino group; and $Z_{21}$ represents the coupling eliminable group of the general formula (I).

6. The silver halide color photographic light-sensitive material of claim 1, wherein the 5-pyrazolone coupler is present in a hydrophilic colloid layer in an amount of $1\times 10^{-3}$ to 1 mole per 1 mole of silver halide present in the same layer or in an adjacent layer.

7. The silver halide color photographic light-sensitive material of claim 1, wherein the silver halide in the silver halide photographic emulsion is silver chloride or silver chlorobromide containing silver chloride in a fraction of at least 90 mol%.

* * * * *